US011911105B2

(12) United States Patent
Kubota et al.

(10) Patent No.: US 11,911,105 B2
(45) Date of Patent: Feb. 27, 2024

(54) MYOPIA PREDICTION, DIAGNOSIS, PLANNING, AND MONITORING DEVICE

(71) Applicant: ACUCELA INC.

(72) Inventors: Ryo Kubota, Seattle, WA (US); Philip M. Buscemi, Mount Pleasant, SC (US)

(73) Assignee: ACUCELA INC., Seattle, WA (US)

( * ) Notice: Subject to any disclaimer, the term of this patent is extended or adjusted under 35 U.S.C. 154(b) by 0 days.

(21) Appl. No.: 18/005,888

(22) PCT Filed: Sep. 30, 2021

(86) PCT No.: PCT/US2021/052893
§ 371 (c)(1),
(2) Date: Jan. 18, 2023

(87) PCT Pub. No.: WO2022/072644
PCT Pub. Date: Apr. 7, 2022

(65) Prior Publication Data
US 2023/0284897 A1 Sep. 14, 2023

Related U.S. Application Data

(60) Provisional application No. 63/198,154, filed on Sep. 30, 2020.

(51) Int. Cl.
*A61B 3/103* (2006.01)
*A61B 3/00* (2006.01)
(Continued)

(52) U.S. Cl.
CPC ............ *A61B 3/103* (2013.01); *A61B 3/0025* (2013.01); *A61B 3/1015* (2013.01); *A61B 3/135* (2013.01); *A61B 3/14* (2013.01); *A61B 3/102* (2013.01)

(58) Field of Classification Search
CPC ...... A61B 3/103; A61B 3/0025; A61B 3/1015; A61B 3/135; A61B 3/14; A61B 3/102
(Continued)

(56) References Cited

U.S. PATENT DOCUMENTS 5,255,274 A 10/1993 Wysocki
5,396,325 A 3/1995 Carome
(Continued)

FOREIGN PATENT DOCUMENTS

CA 3111012 1/2021
CN 105188540 12/2015
(Continued)

OTHER PUBLICATIONS

Bengio, Yoshua, et al., "Curriculum Learning," 8 pages, retrieved from http:/machinelearning.org/archive/icml2009/papers/119.pdf on Jun. 14, 2021.
(Continued)

*Primary Examiner* — Mohammed A Hasan
(74) *Attorney, Agent, or Firm* — FISHERBROYLES, LLP; John K. Shimmick

(57) ABSTRACT

Embodiments of the present disclosure are directed to systems, apparatuses and methods for prediction, diagnosis, planning and monitoring for myopia and myopic progression. In some embodiments, one or more refractive properties of the eye is determined for each of a plurality of retinal locations of the eye. The plurality of locations may comprise a central region, such as a fovea of the eye, or non-foveal region such as a peripheral region or a region of the macula outside the fovea. Measuring the refractive properties of the eye for the plurality of locations may be helpful in diagnosing myopia and other ocular conditions by providing the refractive properties of the eye for locations away from the fovea, such as the peripheral retina.

19 Claims, 8 Drawing Sheets

(51) Int. Cl.
  *A61B 3/10* (2006.01)
  *A61B 3/135* (2006.01)
  *A61B 3/14* (2006.01)
(58) Field of Classification Search
  USPC ........................................................ 351/206
  See application file for complete search history.

(56) References Cited

U.S. PATENT DOCUMENTS

| | | | |
|---|---|---|---|
| 6,053,613 A | 4/2000 | Wei |
| 6,325,512 B1 | 12/2001 | Wei |
| 6,362,919 B1 | 3/2002 | Flanders |
| 6,409,395 B1 | 6/2002 | Wang |
| 6,419,360 B1 | 7/2002 | Hauger |
| 6,445,944 B1 | 9/2002 | Ostrovsky |
| 6,552,796 B2 | 4/2003 | Magnin |
| 6,726,325 B2 | 4/2004 | Xie |
| 6,736,508 B2 | 5/2004 | Xie |
| 6,769,769 B2 | 8/2004 | Podoleanu |
| 6,778,307 B2 | 8/2004 | Clark |
| 7,113,818 B2 | 9/2006 | Podoleanu |
| 7,126,693 B2 | 10/2006 | Everett |
| 7,140,730 B2 | 11/2006 | Wei |
| 7,301,644 B2 | 11/2007 | Knighton |
| 7,324,569 B2 | 1/2008 | Flanders |
| 7,347,548 B2 | 3/2008 | Huang |
| 7,375,818 B2 | 5/2008 | Kawahara |
| 7,391,520 B2 | 6/2008 | Zhou |
| 7,452,077 B2 | 11/2008 | Meyer |
| 7,482,589 B2 | 1/2009 | Flanders |
| 7,542,145 B2 | 6/2009 | Toida |
| 7,594,730 B2 | 9/2009 | Podoleanu |
| 7,602,500 B2 | 10/2009 | Izatt |
| 7,633,623 B2 | 12/2009 | Hatori |
| 7,633,627 B2 | 12/2009 | Choma |
| 7,701,585 B2 | 4/2010 | Hatori |
| 7,761,139 B2 | 7/2010 | Tearney |
| 7,783,337 B2 | 8/2010 | Feldman |
| 7,864,335 B2 | 1/2011 | Terakawa |
| 7,872,759 B2 | 1/2011 | Tearney |
| 7,929,148 B2 | 4/2011 | Kemp |
| 7,954,947 B2 | 6/2011 | Sugita |
| 7,971,999 B2 | 7/2011 | Zinser |
| 7,980,694 B2 | 7/2011 | Keating |
| 7,980,696 B1 | 7/2011 | Taki |
| 7,997,728 B2 | 8/2011 | Huang |
| 7,997,729 B2 | 8/2011 | McLean |
| 8,025,403 B2 | 9/2011 | Maloca |
| 8,049,900 B2 | 11/2011 | Kemp |
| 8,055,107 B2 | 11/2011 | Masuda |
| 8,079,711 B2 | 12/2011 | Stetson |
| 8,123,354 B2 | 2/2012 | Olivier |
| 8,139,226 B2 | 3/2012 | Johnson |
| 8,192,024 B2 | 6/2012 | Yumikake |
| 8,205,991 B2 | 6/2012 | Wei |
| 8,220,924 B2 | 7/2012 | Hanebuchi |
| 8,251,510 B2 | 8/2012 | Kobayashi |
| 8,251,511 B2 | 8/2012 | Stetson |
| 8,282,211 B2 | 10/2012 | Campbell |
| 8,289,522 B2 | 10/2012 | Tearney |
| 8,348,427 B2 | 1/2013 | Buckland |
| 8,348,429 B2 | 1/2013 | Walsh |
| 8,351,665 B2 | 1/2013 | Tearney |
| 8,363,783 B2 | 1/2013 | Gertner |
| 8,403,481 B2 | 3/2013 | Izatt |
| 8,405,834 B2 | 3/2013 | Srinivasan |
| 8,421,855 B2 | 4/2013 | Buckland |
| 8,425,037 B2 | 4/2013 | Uhlhorn |
| 8,442,284 B2 | 5/2013 | Rogers |
| 8,446,593 B1 | 5/2013 | Ellerbee |
| 8,457,440 B1 | 6/2013 | Johnson |
| 8,467,051 B2 | 6/2013 | Flanders |
| 8,474,978 B2 | 7/2013 | Huang |
| 8,500,279 B2 | 8/2013 | Everett |
| 8,526,006 B2 | 9/2013 | Nebosis |
| 8,529,062 B2 | 9/2013 | Buckland |
| 8,594,757 B2 | 11/2013 | Boppart |
| 8,608,314 B2 | 12/2013 | Yoon |
| 8,630,697 B2 | 1/2014 | Meyer |
| 8,665,450 B2 | 3/2014 | Johnson |
| 8,711,366 B2 | 4/2014 | Everett |
| 8,721,078 B2 | 5/2014 | Torii |
| 8,724,870 B2 | 5/2014 | Sekine |
| 8,757,803 B2 | 6/2014 | Everett |
| 8,781,287 B2 | 7/2014 | Flanders |
| 8,794,763 B2 | 8/2014 | Stetson |
| 8,801,184 B2 | 8/2014 | Hacker |
| 8,820,931 B2 | 9/2014 | Walsh |
| 8,836,953 B2 | 9/2014 | Johnson |
| 8,870,376 B2 | 10/2014 | Hogan |
| 8,894,207 B2 | 11/2014 | Hee |
| 8,913,248 B2 | 12/2014 | Sharma |
| 8,922,782 B2 | 12/2014 | Flanders |
| 8,926,097 B2 | 1/2015 | Sakagawa |
| 8,939,582 B1 | 1/2015 | Spaide |
| 8,947,648 B2 | 2/2015 | Swanson |
| 8,953,167 B2 | 2/2015 | Johnson |
| 8,971,360 B2 | 3/2015 | Lewandowski |
| 8,992,018 B2 | 3/2015 | Makihira |
| 8,994,753 B2 | 3/2015 | Nakano |
| 8,998,412 B2 | 4/2015 | Makihira |
| 9,016,862 B2 | 4/2015 | Carnevale |
| 9,025,160 B2 | 5/2015 | Moore |
| 9,025,847 B2 | 5/2015 | Kitamura |
| 9,033,504 B2 | 5/2015 | Everett |
| 9,033,510 B2 | 5/2015 | Narasimha-Iyer |
| 9,044,164 B2 | 6/2015 | Hacker |
| 9,055,891 B2 | 6/2015 | Suehira |
| 9,055,892 B2 | 6/2015 | Narasimha-Iyer |
| 9,060,689 B2 | 6/2015 | Tearney |
| 9,084,562 B2 | 7/2015 | Kakuma |
| 9,095,281 B2 | 8/2015 | Sharma |
| 9,119,562 B2 | 9/2015 | Naba |
| 9,138,141 B2 | 9/2015 | Makihira |
| 9,144,378 B2 | 9/2015 | Suehira |
| 9,149,182 B2 | 10/2015 | Walsh |
| 9,161,690 B2 | 10/2015 | Tomatsu |
| 9,163,929 B2 | 10/2015 | Lim |
| 9,163,930 B2 | 10/2015 | Buckland |
| 9,167,964 B2 | 10/2015 | Everett |
| 9,171,367 B2 | 10/2015 | Yoshihiko |
| 9,176,319 B2 | 11/2015 | Bouma |
| 9,178,330 B2 | 11/2015 | Oh |
| 9,192,294 B2 | 11/2015 | Sharma |
| 9,200,888 B2 | 12/2015 | Jaillon |
| 9,217,707 B2 | 12/2015 | Bajraszewski |
| 9,226,653 B2 | 1/2016 | Torii |
| 9,226,660 B2 | 1/2016 | De Boer |
| 9,241,626 B2 | 1/2016 | Narasimha-Iyer |
| 9,243,885 B2 | 1/2016 | Johnson |
| 9,259,151 B2 | 2/2016 | Murase |
| 9,267,783 B1 | 2/2016 | Sharma |
| 9,273,950 B2 | 3/2016 | Yazdanfar |
| 9,291,446 B2 | 3/2016 | Schneider |
| 9,310,182 B2 | 4/2016 | Goldberg |
| 9,339,186 B2 | 5/2016 | Somani |
| 9,354,038 B2 | 5/2016 | Yasuno |
| 9,373,933 B2 | 6/2016 | Njegovec |
| 9,375,158 B2 | 6/2016 | Vakoc |
| 9,377,293 B2 | 6/2016 | Hauger |
| 9,380,935 B2 | 7/2016 | Iwase |
| 9,408,532 B2 | 8/2016 | Makihira |
| 9,427,147 B2 | 8/2016 | Lujan |
| 9,427,150 B2 | 8/2016 | Muto |
| 9,433,353 B2 | 9/2016 | Hanebuchi |
| 9,468,374 B2 | 10/2016 | Makihira |
| 9,492,077 B2 | 11/2016 | Ebersbach |
| 9,492,079 B2 | 11/2016 | Walsh |
| 9,526,412 B2 | 12/2016 | Yang |
| 9,526,415 B2 | 12/2016 | Fukuma |
| 9,526,425 B2 | 12/2016 | Feldman |
| 9,532,713 B2 | 1/2017 | Levecq |
| 9,545,199 B2 | 1/2017 | Wang |
| 9,584,098 B2 | 2/2017 | Yamanari |

(56) References Cited

U.S. PATENT DOCUMENTS

| | | | |
|---|---|---|---|
| 9,612,105 B2 | 4/2017 | Kemp | |
| 9,615,736 B2 | 4/2017 | Yamashita | |
| 9,633,424 B2 | 4/2017 | Nebosis | |
| 9,649,024 B2 | 5/2017 | Hacker | |
| 9,649,025 B2 | 5/2017 | Jeglorz | |
| 9,671,620 B2 | 6/2017 | Gupta | |
| 9,696,132 B2 | 7/2017 | Jayaraman | |
| 9,702,686 B2 | 7/2017 | Hattersley | |
| 9,778,018 B2 | 10/2017 | Schmoll | |
| 9,778,020 B2 | 10/2017 | Tumlinson | |
| 9,784,559 B2 | 10/2017 | Huber | |
| 9,812,846 B2 | 11/2017 | Yun | |
| 9,869,542 B2 | 1/2018 | Goldberg | |
| 9,897,538 B2 | 2/2018 | Tearney | |
| 9,915,520 B2 | 3/2018 | Cable | |
| 9,939,659 B2 | 4/2018 | Gupta | |
| 9,948,061 B2 | 4/2018 | Njegovec | |
| 9,977,184 B1 | 5/2018 | Wong | |
| 9,978,159 B2 | 5/2018 | Kraus | |
| 9,993,153 B2 | 6/2018 | Chong | |
| 10,045,692 B2 | 8/2018 | Tumlinson | |
| 10,049,470 B2 | 8/2018 | Pintal | |
| 10,098,537 B2 | 10/2018 | Iwase | |
| 10,114,232 B2 | 10/2018 | Gupta | |
| 10,327,631 B2 | 6/2019 | Huang | |
| 10,413,175 B2 | 9/2019 | Yun | |
| 10,478,058 B2 | 11/2019 | Cheng | |
| 10,568,501 B2 | 2/2020 | Boss | |
| 10,595,723 B2 | 3/2020 | Meznaric | |
| 10,610,096 B2 | 4/2020 | Scheibler | |
| 10,912,456 B2 | 2/2021 | Brennan | |
| 10,952,607 B2 | 3/2021 | Scheibler | |
| 10,959,613 B1 | 3/2021 | Kubota | |
| 11,357,401 B2 | 6/2022 | Oggenfuss et al. | |
| 11,369,266 B2 | 6/2022 | Kubota | |
| 11,393,094 B2 | 7/2022 | Wyder | |
| 11,497,396 B2 | 11/2022 | Kubota | |
| 11,694,353 B2 * | 7/2023 | Ninan | G06T 7/593 382/154 |
| 2003/0011745 A1 * | 1/2003 | Molebny | A61B 3/1015 351/215 |
| 2004/0246441 A1 | 12/2004 | Stark | |
| 2004/0257529 A1 | 12/2004 | Thomas | |
| 2005/0018133 A1 | 1/2005 | Huang | |
| 2005/0140981 A1 | 6/2005 | Waelti | |
| 2006/0131488 A1 | 6/2006 | Thingbo | |
| 2006/0152106 A1 | 7/2006 | Yan | |
| 2006/0244339 A1 | 11/2006 | Mazz | |
| 2007/0002452 A1 * | 1/2007 | Munro | G02B 3/0025 359/627 |
| 2007/0076217 A1 | 4/2007 | Baker | |
| 2007/0127349 A1 | 6/2007 | Hotta | |
| 2007/0183643 A1 | 8/2007 | Jayaraman | |
| 2007/0230856 A1 | 10/2007 | Yamazaki | |
| 2007/0263171 A1 | 11/2007 | Ferguson | |
| 2008/0100612 A1 | 5/2008 | Dastmalchi | |
| 2008/0117427 A1 | 5/2008 | Teramura | |
| 2008/0181263 A1 | 7/2008 | Bouma | |
| 2008/0296480 A1 | 12/2008 | Haber | |
| 2009/0002631 A1 | 1/2009 | Campbell | |
| 2009/0123044 A1 | 5/2009 | Huang | |
| 2009/0141237 A1 | 6/2009 | Izatt | |
| 2009/0244485 A1 | 10/2009 | Walsh | |
| 2010/0110376 A1 | 5/2010 | Everett | |
| 2010/0110377 A1 | 5/2010 | Maloca | |
| 2011/0043757 A1 | 2/2011 | Everett | |
| 2011/0080561 A1 | 4/2011 | Hayashi | |
| 2011/0157554 A1 | 6/2011 | Kawai | |
| 2011/0164633 A1 | 7/2011 | Moench | |
| 2011/0299034 A1 | 12/2011 | Walsh | |
| 2012/0033227 A1 | 2/2012 | Bower | |
| 2012/0092616 A1 | 4/2012 | Peyman | |
| 2012/0300216 A1 | 11/2012 | Johnson | |
| 2012/0327365 A1 | 12/2012 | Makihira | |
| 2013/0010259 A1 | 1/2013 | Carnevale | |
| 2013/0010302 A1 | 1/2013 | Sharma | |
| 2013/0016360 A1 | 1/2013 | Ensher | |
| 2013/0103014 A1 | 4/2013 | Gooding | |
| 2013/0158392 A1 | 6/2013 | Papac | |
| 2013/0235343 A1 | 9/2013 | Hee | |
| 2013/0250241 A1 | 9/2013 | Everett | |
| 2014/0028997 A1 | 1/2014 | Cable | |
| 2014/0112562 A1 | 4/2014 | Yamakawa | |
| 2014/0121508 A1 | 5/2014 | Latimer | |
| 2014/0125987 A1 | 5/2014 | Flanders | |
| 2014/0218745 A1 | 8/2014 | Hattersley | |
| 2014/0241605 A1 | 8/2014 | Izatt | |
| 2014/0268050 A1 | 9/2014 | Jayaraman | |
| 2014/0268169 A1 | 9/2014 | Jayaraman | |
| 2014/0269796 A1 | 9/2014 | Geske | |
| 2014/0285812 A1 | 9/2014 | Levitz | |
| 2014/0307078 A1 | 10/2014 | Charles | |
| 2014/0307753 A1 | 10/2014 | Minneman | |
| 2014/0340689 A1 | 11/2014 | Namati | |
| 2014/0347632 A1 | 11/2014 | Mordaunt | |
| 2015/0010031 A1 | 1/2015 | Makino | |
| 2015/0018674 A1 | 1/2015 | Scott | |
| 2015/0055089 A1 | 2/2015 | Aono | |
| 2015/0062532 A1 | 3/2015 | Sharma | |
| 2015/0085253 A1 | 3/2015 | Walsh | |
| 2015/0109579 A1 | 4/2015 | Orlowski | |
| 2015/0110376 A1 | 4/2015 | Gessner | |
| 2015/0198431 A1 | 7/2015 | Uchida | |
| 2015/0216408 A1 | 8/2015 | Brown | |
| 2015/0216412 A1 | 8/2015 | Hillmann | |
| 2015/0230705 A1 | 8/2015 | Kato | |
| 2015/0327761 A1 | 11/2015 | Narasimha-Iyer | |
| 2015/0327762 A1 | 11/2015 | Isogai | |
| 2016/0000368 A1 | 1/2016 | Wang | |
| 2016/0007857 A1 | 1/2016 | Wang | |
| 2016/0025478 A1 | 1/2016 | Johnson | |
| 2016/0040976 A1 | 2/2016 | Berkeley | |
| 2016/0040977 A1 | 2/2016 | An | |
| 2016/0040978 A1 | 2/2016 | Boppart | |
| 2016/0081545 A1 | 3/2016 | Hauger | |
| 2016/0082129 A1 | 3/2016 | Peters | |
| 2016/0106310 A1 | 4/2016 | Moriguchi | |
| 2016/0106312 A1 | 4/2016 | Moriguchi | |
| 2016/0106314 A1 | 4/2016 | Everett | |
| 2016/0128565 A1 | 5/2016 | Meznaric | |
| 2016/0166143 A1 | 6/2016 | Goto | |
| 2016/0206190 A1 | 7/2016 | Reisman | |
| 2016/0212404 A1 | 7/2016 | Maiello | |
| 2016/0242638 A1 | 8/2016 | Durbin | |
| 2016/0252340 A1 | 9/2016 | Hollenbeck | |
| 2016/0262609 A1 | 9/2016 | Cai | |
| 2016/0270656 A1 | 9/2016 | Samec | |
| 2016/0321578 A1 | 11/2016 | Tachikawa | |
| 2016/0338589 A1 | 11/2016 | Carrasco-Zevallos | |
| 2016/0367129 A1 | 12/2016 | Coelho | |
| 2016/0367132 A1 | 12/2016 | Yun | |
| 2017/0007182 A1 | 1/2017 | Samec | |
| 2017/0020387 A1 | 1/2017 | Fingler | |
| 2017/0049318 A1 | 2/2017 | Walsh | |
| 2017/0055829 A1 | 3/2017 | Tan | |
| 2017/0065169 A1 | 3/2017 | Fukasawa | |
| 2017/0074640 A1 | 3/2017 | Cable | |
| 2017/0102223 A1 | 4/2017 | Izatt | |
| 2017/0105618 A1 | 4/2017 | Schmoll | |
| 2017/0140560 A1 | 5/2017 | Kraus | |
| 2017/0156583 A1 | 6/2017 | Seesselberg | |
| 2017/0205223 A1 | 7/2017 | Cable | |
| 2017/0227350 A1 | 8/2017 | Sarunic | |
| 2017/0231489 A1 | 8/2017 | Fujimori | |
| 2017/0236255 A1 | 8/2017 | Wetzstein | |
| 2017/0241763 A1 | 8/2017 | Wang | |
| 2017/0258321 A1 | 9/2017 | Dastmalchi | |
| 2017/0268987 A1 | 9/2017 | Swanson | |
| 2017/0276471 A1 | 9/2017 | Jiang | |
| 2017/0280993 A1 | 10/2017 | Fukuhara | |
| 2017/0311795 A1 | 11/2017 | Sumiya | |
| 2017/0356740 A1 | 12/2017 | Ansari | |
| 2018/0012359 A1 | 1/2018 | Prentasic | |
| 2018/0031363 A1 | 2/2018 | Johnson | |

(56) References Cited

U.S. PATENT DOCUMENTS

| | | |
|---|---|---|
| 2018/0051978 A1 | 2/2018 | Flanders |
| 2018/0055358 A1 | 3/2018 | Nakajima |
| 2018/0064331 A1 | 3/2018 | Naba |
| 2018/0084994 A1 | 3/2018 | Su |
| 2018/0125354 A1 | 5/2018 | Pulaski |
| 2018/0135962 A1 | 5/2018 | Murata |
| 2018/0156598 A1 | 6/2018 | Cable |
| 2018/0157924 A1 | 6/2018 | Hogan |
| 2018/0168445 A1 | 6/2018 | Horn |
| 2018/0206716 A1 | 7/2018 | Chong |
| 2018/0271363 A1 | 9/2018 | Scheibler |
| 2018/0289256 A1 | 10/2018 | Murata |
| 2019/0365220 A1 | 12/2019 | Frisken |
| 2019/0380574 A1 | 12/2019 | Chen |
| 2020/0093363 A1 | 3/2020 | Saika |
| 2020/0196858 A1 | 6/2020 | Scheibler |
| 2020/0234080 A1 | 7/2020 | Ciller Ruiz |
| 2020/0342595 A1 | 10/2020 | Jia |
| 2020/0372632 A1 | 11/2020 | Chauhan |
| 2021/0127969 A1 | 5/2021 | Oggenfuss |
| 2021/0196113 A1 | 7/2021 | Copland |
| 2021/0386285 A1 | 12/2021 | Walsh |
| 2022/0276495 A1* | 9/2022 | Pu .................... G02B 27/0172 |

FOREIGN PATENT DOCUMENTS

| | | |
|---|---|---|
| CN | 105263415 | 1/2016 |
| CN | 105792728 | 7/2016 |
| DE | 102016121246 | 5/2018 |
| EP | 2725508 | 4/2014 |
| EP | 2759254 | 7/2014 |
| EP | 2892413 | 7/2015 |
| JP | 201172716 | 4/2011 |
| JP | 201483266 | 5/2014 |
| JP | 2016514828 | 5/2016 |
| WO | 9320743 | 10/1993 |
| WO | 2009120544 | 10/2009 |
| WO | 2010117386 | 10/2010 |
| WO | 2015082001 | 6/2015 |
| WO | 2015116981 | 8/2015 |
| WO | 2015120055 | 8/2015 |
| WO | 2015192117 | 12/2015 |
| WO | 2016040534 | 3/2016 |
| WO | 2016073840 | 5/2016 |
| WO | 2016115387 | 7/2016 |
| WO | 2016125474 | 8/2016 |
| WO | 2016127140 | 8/2016 |
| WO | 2016148569 | 9/2016 |
| WO | 2016178298 | 11/2016 |
| WO | 2016179431 | 11/2016 |
| WO | 2016196463 | 12/2016 |
| WO | 2016203245 | 12/2016 |
| WO | 2017002379 | 1/2017 |
| WO | 2017025583 | 2/2017 |
| WO | 2017046225 | 3/2017 |
| WO | 2017048832 | 3/2017 |
| WO | 2017165793 | 9/2017 |
| WO | 2017176301 | 10/2017 |
| WO | 2017206929 | 12/2017 |
| WO | 2017216242 | 12/2017 |
| WO | 2018086173 | 5/2018 |
| WO | 2018089682 | 5/2018 |
| WO | 2018105549 | 6/2018 |
| WO | 2018116128 | 6/2018 |
| WO | 2018119077 | 6/2018 |
| WO | 2019210079 | 10/2019 |
| WO | 2019246412 | 12/2019 |
| WO | 2020036182 | 2/2020 |
| WO | 2020160839 A1 | 8/2020 |
| WO | 2021134087 | 7/2021 |
| WO | 2022032260 | 2/2022 |
| WO | 2022035809 | 2/2022 |
| WO | 2022056515 | 3/2022 |
| WO | 2022204622 | 9/2022 |

OTHER PUBLICATIONS

Bertera, J.H., et al., "Stabilized Retinal Mapping of Known Retinal Loci," Proceedings of the Annual Northeast Bioengineering Conference, IEEE, vol. Conf. 14, No. 1988, XP000010509 (Mar. 10, 1988).

Girish et al. Segmentation of Intra-Retinal Cysts From Optical Coherence Tomography Images Using a Fully Convolutional Neural Network Model. IEEE Journal of Biomedical and Health Informatics, vol. 23, No. 1, Jan. 2019, pp. 296-304 (Year: 2019).

Haglund, Erik, et al., "Multi-wavelength VCSEL arrays using high-contrast gratings," Proc. of SPIE vol. 10113, 7 pages (2017).

Huang, et al., "Optical coherence tomograph," Science, 254(5035):1178-1181 (Nov. 22, 1991).

Huang, Huimin, et al., "UNET 3+: A Full-Scale Connected UNET for Medical Image Segmentation," 5 pages, retrieved from https://arxiv.org/ftp/arxiv/papers/2004/2004.08790.pdf on Jun. 14, 2021.

International Search Report and Written Opinion for PCT/US2021/052893, 22 pages (dated Feb. 7, 2022).

Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).

Khan, Zuhaib, et al., "High-brightness and high-speed vertical-cavity surface-emitting laser arrays," Optica, 7(4):267-275 (Apr. 2020).

Kolb, Jan Philip, et al., "High-resolution retinal swept source optical coherence tomography with an ultra-wideband Fourier-domain mode-locked laser at MHz A-scan rates," Biomedical Optics Express, 9(1):120-130 (2018).

Mishra, Z., et al., "Automated Retinal Layer Segmentation Using Graph-based Algorithm Incorporating Deep-learning-derived Information," Sci Rep. 10(1):9541 (2020).

Moon, S., et al., "VCSEL-based swept source for low-cost optical coherence tomography", Biomedical Optics Express, 8(2):1110-1121 (Feb. 1, 2017).

ORR. Notal Vision—Home-Based Optical Coherence Tomograph (OCT). Slide deck (11 pgs.) (Nov. 9, 2017).

Pierro, L., et al., "Macular Thickness Interoperator and Intraoperator Reproducibility in Healthy Eyes Using 7 Optical Coherence Tomography Instruments," American Journal of Ophthalmology, 150(2): 199-204, XP027174249 (Aug. 1, 2010).

Sanghoon, Kim, et al., "Design and implementation of a low-cost, portable OCT system," 9(3):1232-1243 (Mar. 1, 2018).

WO 2020/036182 A1 machine translation from Japanese to English (132 pages).

Zara, J.M., et al., "Electrostatic micromachine scanning mirror for optical coherence tomography," Optics Letters, 28(8):628-630 (Apr. 15, 2003).

* cited by examiner

MYOPIA PREDICTION, DIAGNOSIS, PLANNING, AND MONITORING DEVICE

RELATED APPLICATIONS

This application is a 371 national phase of PCT/US2021/052893, filed Sep. 30, 2021, published as WO 2022/072644 on Apr. 7, 2022, and claims the benefit under 35 U.S.C. § 119(e) of U.S. Provisional Patent Application No. 61/198,154, filed Sep. 30, 2020, the entire disclosure of which is incorporated herein by reference.

BACKGROUND

Myopia, also known as near-sightedness, is a visual disorder that is frequently progressive and worsens through adolescence and early adulthood. It is characterized by the ability to see objects clearly at nearer distances, but at farther distances objects become blurry. Work in relation to the present disclosure suggests that this may result from the eye being somewhat elongated, so that images of objects are not focused at the retina. In some myopic persons, the axial dimension or axis of the eye increases over time, with the result of worsening near-sightedness. It has been demonstrated that the progression of myopia in some patients can be slowed or stopped by providing stimuli consisting of an image that is defocused in front of the retina, a technique referred to as myopic defocus.

Work in relation to the present disclosure suggests that the refractive error of the retina may play a role in the progression of myopia, and prior approaches to predicting myopia and myopic progression to provide appropriate diagnosis and treatment can be less than ideal in at least some instances. For example, some prior measurement approaches only account of refractive errors of the central vision. This approach can be less than ideal because it does not account for refractive errors of the retinal areas outside the fovea and differences in refractive error between the central retina, e.g. the fovea, and areas outside the fovea, e.g. the peripheral retina. For example, at least some prior auto-refractors and wavefront measurement systems measure the refraction and wavefront of the eye for light focused to the fovea without measuring the refractive properties of the eye with respect to the areas outside the fovea such as the peripheral retina. Although some of these devices such as wavefront aberrometers map the wavefront error of the eye over the pupil, this mapping over the pupil is typically with respect to the fovea and not with respect to the outer regions of the retina outside the fovea such as the peripheral retina.

In light of the above improved methods and apparatus are needed that ameliorate at least some of the aforementioned limitations of the prior approaches to measuring and treating refractive error.

SUMMARY

Embodiments of the present disclosure are directed to systems, apparatuses and methods for prediction, diagnosis, planning and monitoring for myopia and myopic progression. In some embodiments, one or more refractive properties of the eye is determined for each of a plurality of locations of the eye. The plurality of locations may comprise a central region, such as a fovea of the eye, and a location outside the fovea, such as a region of peripheral retina or a region of the macula outside the fovea. Measuring the refractive properties of the eye for the plurality of locations may be helpful in diagnosing myopia and other ocular conditions by providing the refractive properties of the eye for locations away from the fovea, such as the peripheral retina and other locations outside the fovea.

In some embodiments, an apparatus to measure relative refractive properties of an eye comprises one or more light sources configured to emit light. Projection optics are arranged to project the light emitted by the one or more light sources onto a central location of the retina and a peripheral location of the retina. Imaging optics are arranged to generate a plurality of images from the light projected onto the fovea location of the retina and the peripheral location of the retina. An imaging device configured to capture the plurality of images from the efferent optics. A processor is coupled to the imaging device, and the processor configured to determine refractive properties of the eye for the central location of the retina and the peripheral location of the retina In some embodiments, a method of measuring refractive properties of an eye, the method comprises projecting a first spot of light onto a central location of a retina of the eye. A first image of the first spot of light on the central location is captured. A second spot of light is projected onto a location of the retina away from the central location. A second image of the second spot of light outside the fovea such as on the peripheral retina or the macula outside the fovea is captured. A refraction of the eye is determined at the central location of the retina and the location away from the fovea such as the peripheral retina or the macula outside the fovea.

In some embodiments, refractive properties of the eye that can be measured by the instrument include axial length of the eye. Axial length of the eye may be measured centrally, and over a range of eccentricities up to +/−6.0 degrees or more.

In some embodiments, a method of generating refractive maps of an eye comprises fogging the eye with a far stimulus to provide a far vision accommodation of the eye and mapping the refractive error of the eye in a far vision configuration and providing a near vision stimulus to provide near visional accommodation and mapping the refractive error of the eye in a near vision configuration. A first refractive map of the patient's eye is generated with the far vision accommodation of the eye. The patient's eye is stimulated with a near stimulus to provide a near vision accommodation of the eye. A second refractive map of the patient's eye is generated with the near vision accommodation of the eye. The first refractive map of the patient's eye is compared with the second refractive map of the patient's eye.

INCORPORATION BY REFERENCE

All patents, applications, and publications referred to and identified herein are hereby incorporated by reference in their entirety and shall be considered fully incorporated by reference even though referred to elsewhere in the application.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

Figure 1:
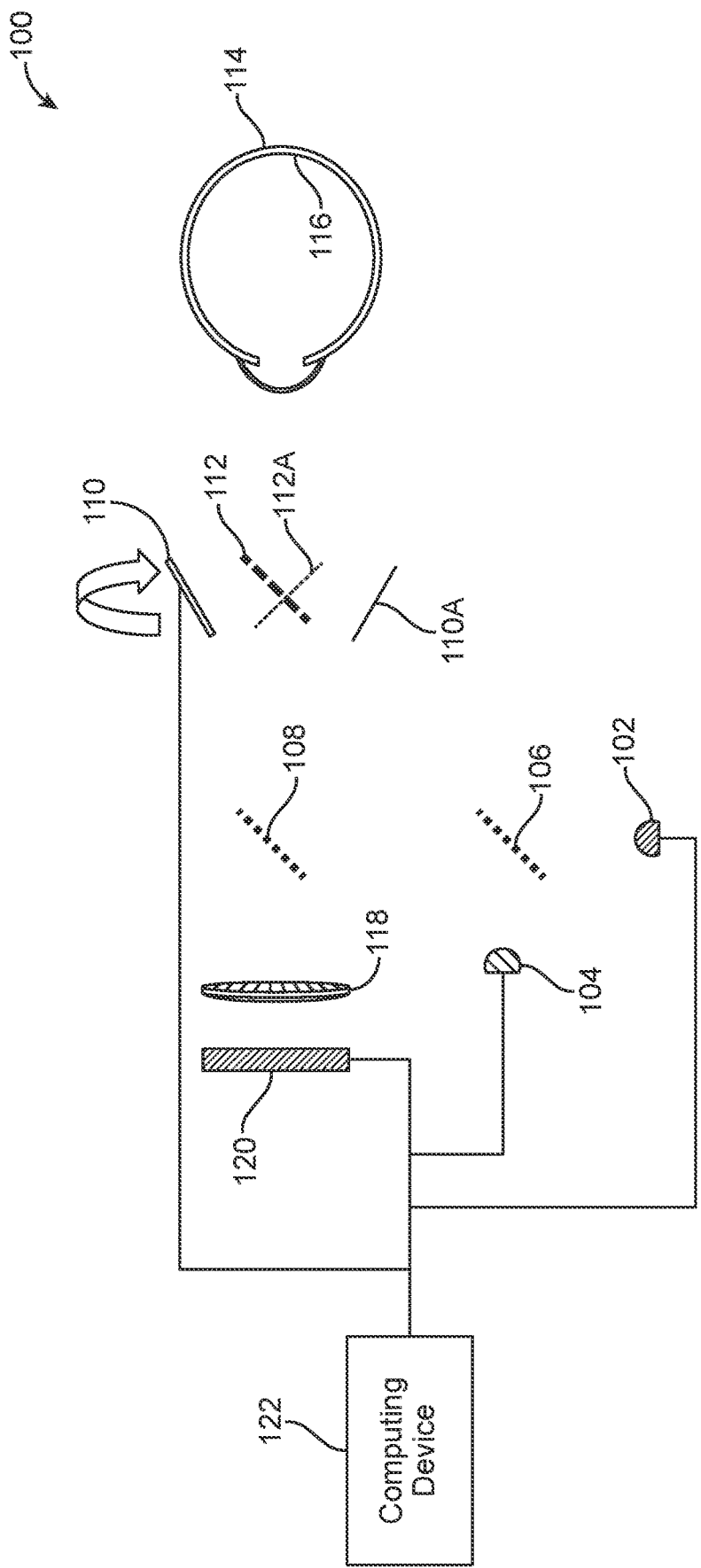
FIG. 1 shows a diagram of a system for mapping the refractive error the eye at central and non-central locations of the retina, such as foveal locations and non-foveal locations of the retina, in accordance with some embodiments.

The following detailed description and provides a better understanding of the features and advantages of the inventions described in the present disclosure in accordance with the embodiments disclosed herein. Although the detailed description includes many specific embodiments, these are provided by way of example only and should not be construed as limiting the scope of the inventions disclosed herein.

The presently disclosed methods, devices and systems are well suited for incorporation into prior art devices such as wavefront measurement devices and auto-refractors and may comprise one or more components of commercially available auto-refractors and wavefront measurement systems. Although specific reference is made to auto-refractors and wavefront aberrometers herein, the disclosed systems, apparatus and methods are suited for use with, or incorporation into, other devices or systems. A person of ordinary skill in the art will readily appreciate how one or more of the disclosed components or elements may be incorporated with auto-refractors and wavefront aberrometers or other systems or devices, based on the teachings provided herein. For example, one or more components of a commercially available Hartmann-Shack wavefront system such as a lenslet array and detector may be modified in accordance with the present disclosure. Alternatively or in combination, a scanning slit auto-refractor can be modified in accordance with the present disclosure.

Although the presently disclosed systems, methods and apparatus can be used for myopia prediction, diagnosis, planning, and monitoring, the presently disclosed methods and apparatus are well suited to measure any type of refractive error of the eye and retina. While reference is made to the measurement of refractive errors of the eye, the presently disclosed methods, devices and systems are well suited for use in many fields and optical systems that form images of objects, such as optical microscopy, astronomy, optical metrology.

In some embodiments, the systems, methods and apparatus can be used to track progression of myopia or reversal of myopia in a patient may be tracked. For example, a measuring device may be used to measure the axial length of the patient's eye before and during treatment. The axial length of the eye may be measured centrally and/or over a range of eccentricates of up to +/−6.0 degrees or more. For example, the length may be measured at the fovea and over a range of eccentricates of up to +/−6.0 degrees around the fovea. Alternatively or in combination, the axial length can be measured at locations within a range from 0 degrees to 10 degrees or more eccentric from the fovea, for example measured at 5 degrees eccentric to the fovea and at 10 degrees eccentric to the fovea. The axial length may be measured before providing any of the contact lenses discussed herein and then measured one or more times during treatment with any of the contact lenses discussed herein. By tracking the measurements, a medical professional can make treatment decisions for the patient, such as modifying or concluding treatment.

Unless indicated otherwise, the described embodiments comprise one or more light sources and one or more optical elements to project and transmit afferent light onto the retina of a patient and to receive efferent light from the retina with an imaging device. The one or more light sources may include light emitting diodes (LED), organic light emitting diodes (OLED), LED lasers, a phosphorescent LEDs or a plurality of LEDs lasers, for example. The light sources may emit one or more different wavelengths of light. The optical elements may include one or more filters, lenses, dichroic mirrors, beam splitters, lens arrays, lenslets, micro lenslets, and micro lenslet arrays, and a partial mirror (or set of partial mirrors). The mirrors may be a flat mirror, partial mirror, or concave mirror. Lenses may have one or more flat, concave, or convex surfaces. The imaging device may be a charge coupled device (CCD), a complementary metal-oxide-semiconductor sensor (CMOS sensor), or other imaging device. The imaging device may be a monochrome imaging device or color imaging device and may include one or more filters.

Logic to carry out the methods described herein may be implemented in the form of a computing device and/or processor programmed with a set of executable instructions to control the operation of the light sources, imaging device, and optical devices, such as movement of mirrors.

FIG. 1 shows a diagram of a system 100 for mapping the refractive error of the eye 114 at a central location of the retina 116 and another location of the retina away from the central location. The location away from the central location may comprise a location of the macula outside the fovea or a location on the peripheral retina, for example. The refractive error of light to the central location, e.g. the fovea, and the corresponding refractive error of light to each of a plurality of locations of the retina outside the central location, e.g. the macula outside the fovea or the peripheral retina can be measured. The system may include a computing device 122 coupled to an imaging device 120 and more light sources 102, 104. The system 100 may also include one or more optical devices, such as beam splitters 106, 108, rotating mirror 110 and dichroic mirror 112. The computing device 122 may be operationally coupled to one or more of the optical devices. For example, the computing device 122 may be coupled to the rotating mirror 110 in order to control the rotation of the mirror 110. In some embodiments, light source 102 is configured to project light to a central location of the retina, e.g. the fovea, and light source 104 is configured to project light to one or more locations of the retina away from the fovea, e.g. the peripheral retina, in order to measure refractive error of the eye at the fovea and each of the one or more locations of the eye away from the fovea, e.g. refractive error at one or more locations of areas of the retina other than the fovea, such as the peripheral retina or areas of the macula outside the fovea.

The light sources 102, 104 may include light emitting diodes (LED), organic light emitting diodes (OLED), LED lasers, phosphorescent LEDs or a plurality of LED lasers. Each light source may omit one or more wavelengths of light. For example, in some embodiments, light source 104 may emit a color in the red visible light spectrum while light source 102 may emit light in a blue light spectrum. In some embodiments, light source 104 and light source 106 may emit light of different wavelengths within the near infrared range, for example, in a range between 800 nm and 1000 nm. The wavelengths of the light sources 102, 104 may differ by at least 20 nm, 30 nm, 40 nm, 50 nm, 60 nm, 70 nm, 80 nm, 90 nm, or 100 nm. The difference in wavelengths emitted by light sources 102, 104 may be determined in part by one or more of the bandwidth of the light emitted by each light source and the filtering capabilities of any filters within the system 100. For example, if light sources 102, 104 emit monochromatic light within a range of 10 nm of a set value and filters used to filter light on the imaging device 120 are configured to filter light within a range of 20 nm of a set value then the light sources 102, 104 may each emit monochromatic light at wavelengths at least 30 nm apart from each other.

The light sources may be controlled by the computing device 122 such that they emit light simultaneously or sequentially. For example, in some embodiments the light sources 102, 104 emit light of the same or similar wavelengths, and the light sources may be controlled such that they emit light sequentially. In some embodiments, light sources 102, 104 emit light of different wavelengths, and the light sources may be controlled such that they emit light simultaneously, for example.

In some embodiments the light sources 102, 104 may be polarized at different angles. In such embodiments, a polarizing filter may be used to selectively filter light of the same wavelength that may be simultaneously emitted by the light sources 102, 104, for example. Although reference is made to the simultaneous emission of light, the light sources and optics configured for this can alternatively be configured to emit light sequentially.

Light emitted by the one or more light sources, such as light sources 102, 104 may travel through or be reflected by one or more beam splitters, such as beam splitters 106, 108, that may serve to transmit the light emitted by light sources 102, 104 onto the retina 116 of a patient's eye 114.

The beam splitters can be configured to separate light in many ways, and may comprise one or more of polarizing beam splitters, wavelength selective mirrors or partially reflective mirrors, for example. In some embodiments, the beam splitter is configured to separate a light beam into two separate light wavelengths, for example with one or more of dichroic filters, prism, gratings or other means. In some embodiments, beam splitter 106 may be formed from two triangular glass prisms glued together such that at the interface between the two prisms a portion of the incident light is transmitted through the interface while a portion of the light is reflected off the interface. In some embodiments, a half-silvered mirror may be used as a beam splitter. A half-silvered mirror may comprise a mirror in which a partially transparent reflective coating is formed on an optical substrate, for example. The partially transparent reflective coating allows a portion of a light to pass through the mirror, e.g. a half silvered mirror, while another portion of light is reflected by the half-silvered mirror. In some embodiments, other types of beam splitters may be used such as dichroic beam splitters.

Light emitted by the one or more light sources may also be reflected by one or more mirrors such as rotating mirror 110 and dichroic mirror 112. The dichroic mirror 112 may be used in implementations of system 100 wherein different wavelengths of light are emitted by light emitters 102, 104. A dichroic mirror, such as dichroic mirror 112, uses the thin film interference in order to allow light of a particular wavelength or band of wavelengths to be reflected off the mirror while light of other wavelengths or bands of wavelengths is transmitted through the mirror. In system 100, the properties of the dichroic mirror may be selected such that the dichroic mirror reflects light of a first wavelength emitted from a first of the light sources 102, 104 while the dichroic mirror transmits light of a second wavelength emitted from a second of the light sources 102, 104. The dichroic mirror may be arranged such that it transmits light into the central retina such, as the fovea of the eye. The dichroic mirror may also comprise a rotating mirror. For example, in some embodiments the dichroic mirror may be coupled to the computing device 122 with an actuator, e.g. a motor, such that the computing device may control the rotation of the dichroic mirror about the optical axis of the eye. The optical axis of the eye may correspond to an axis passing through the center of the primary lens and pupil and extending to the fovea of the patient's eye. Dichroic mirror 112 is shown in position 112A wherein the dichroic mirror 112 is configured to be rotated 180° about the optical axis of the eye.

The rotating mirror 110 may comprise a front surface or first surface mirror wherein the reflective surface is coated on a backing, such as an optical substrate, in a manner that incident light reflects off the reflective surface without passing through the optical substrate. Alternatively, in some embodiments the rotating mirror may comprise a second surface mirror wherein the reflective surface is coated on an optical substrate in a manner that incident light passes through the optical substrate before being reflected off reflected surface. The rotating mirror 110 may be arranged such that it reflects light onto a non-central portion of the retina about the fovea, such as the peripheral retina or a location of the macula outside the fovea. In some embodiments, the mirror 110 rotates about an optical axis of the eye such that it reflects light toward locations of the retina away from the fovea, such as locations of the peripheral retina or the macula outside the fovea. For example, the rotating mirror 110 is shown in position 110A wherein it has rotated 180° about the optical axis of the eye. The rotating mirror 110 may work in combination with the rotating dichroic mirror 112 in order to project the light onto a plurality of locations of the patient's retina outside the fovea, as described in more detail below with reference to FIG. 2.

Although reference is made to a moving mirror, in some embodiments, different locations of a fixation light are used to measure the refractive properties of the eye at the central location and the non-central location. For example, in some embodiments the fixation light is aligned with the optical axis of the measurement system to measure the fovea for a first measurement and then is inclined at an angle to the measurement axis of the optical system measure the retina at a non-central location corresponding to an angle of the fixation light with the measurement axis.

The lenslet array 118 may comprise a plurality of lenslets arranged in an array such as a two-dimensional array. Each individual lenslet of the lenslet array 118 focuses the light reflected off the retina 114 from a different perspective of any of the other lenslets of the lens array 118, and each lenslet of the array may correspond to a different location of a pupil of the eye. Each individual lenslet of the lens array 118 focuses the image from its respective perspective onto an imaging location on the imaging device 120, such as a two dimensional sensor array, e.g. a complimentary-metal-oxide semiconductor (CMOS) sensor array. As described in more detail below, the location of the point of light projected onto the imaging device provides information regarding the refractive properties of the patient's eye.

The lenslet array 118 may be positioned between the patient's eye 114 and the imaging device 120. Also, additional optical components such as lenses can be used to image the pupil of the eye onto the lenslet array, for example.

The lenslet array 118 can be configured in many ways, and may comprise one or more of gradient index ("GRIN") lenses, geometrically curved spherical lenses, diffractive optics or crossed cylindrically shaped rods, for example. In some embodiments, the lenslet array comprises a plurality of lenslets formed on an optical substrate. In some embodiments, the lenslet array 118 may include a plurality of individual lenslets held together in a two-dimensional array by a frame or other structural device. The two-dimensional array formed by the lenslets may be arranged in a square or rectangular array wherein the individual lenslets are arranged in a plurality of rows and columns. In some embodiments, the two-dimensional array may be circular, wherein the lenslets are arranged in concentric circular patterns about a central axis. The central axis may correspond to the axis of the patient's eye. In some embodiments, the array may comprise a hexagonal array of lenslets.

The lenslets may be formed from a diffractive optical structure, echelettes, Fresnel lenses, or curved external surfaces. Each microlens may have a size, for example a diameter or length of a side, of between 1 μm and 1 mm, more preferably between 50 μm and 200 μm. In some embodiments, the lenslets may be round, square, or other shape. In some embodiments, the pitch or distance between each microlens may be between 1 μm and 1 mm, for example between 50 μm and 200 μm. In some embodiments, a mask, such as a chrome mask, may be applied to the substrate between the lenslets in order to increase the contrast of the image formed by the micro lenslet array 118.

The imaging device 120 may include an image sensor such as a CCD image sensor or a CMOS image sensor. The imaging device may be a monochrome imaging device or color imaging device and may include one or more filters. A color imaging device may have one or more color filters or filter arrays integrated into the device such as a Bayer, RGBW, or RGBE filter array.

The computing device 122 may include a processor, memory, and instructions stored within the memory to execute the methods discussed herein. The processor may include input and output devices for controlling the operation of the light sources 102, 104, the imaging device 120, and the optical devices such as the rotating mirror 112, the lenslets array 118, and the beam splitters 106, 108.

Figure 2:
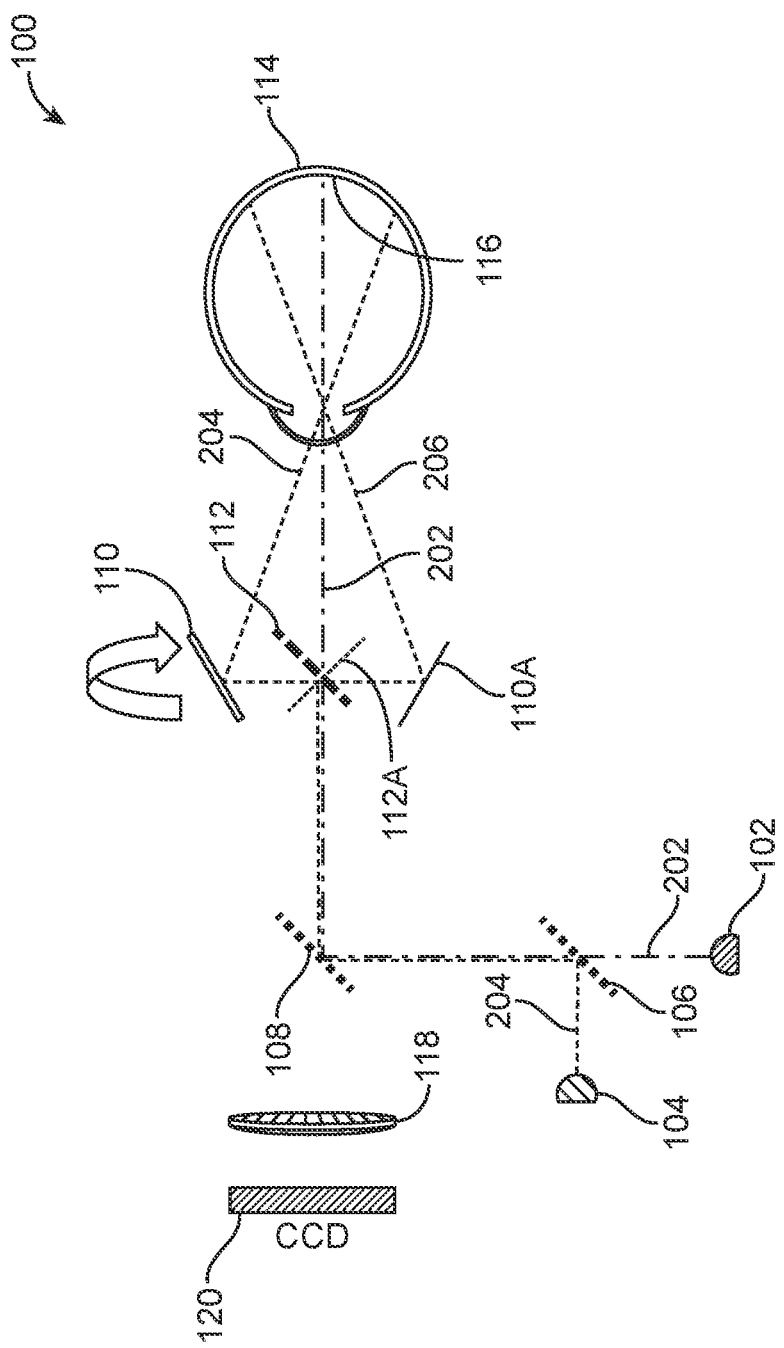
FIG. 2 shows a diagram of the afferent light path of the system of FIG. 1, in accordance with some embodiments.

FIG. 2 shows a diagram of the afferent light paths 202, 204 of the system 100 of FIG. 1 for mapping the refractive error of the patient's eye. In some embodiments, during a first time period, light source 102 emits a beam of light along afferent light path 202. The light beam travels along the afferent light path 202 through the beam splitter 106 and is then reflected off a surface of the beam splitter 108. The beam splitter 108 may be arranged such that light passing through beam splitter 106 is reflected off the beam splitting surface in a direction substantially parallel to the optical axis of the patient's eye. From the beam splitter 108, the light continues along afferent light path 202 and passes through the mirror such as dichroic mirror 112. In such embodiments, the dichroic mirror allows light of the wavelength emitted by light source 102 to be transmitted therethrough. After passing through the mirror 112 the light continues to travel along afferent light path 202 through the patient's lens and cornea and illuminates a spot on the fovea of the patient's retina 116. As discussed herein, dichroic mirror 112 may rotate about the central axis of the patient's eye or about the afferent light path 202. However, in some embodiments the rotation of the dichroic mirror 112 may not substantially affect the transmission of the light from light source 102 into the patient's eye and on to the fovea.

In some embodiments, light from light source 102 may pass through the beam splitter 106 and be reflected off beam splitter 108 along afferent light path 202, as discussed above, however upon reaching the dichroic mirror light from the light source 102 the light may be reflected off the dichroic mirror 112. In such embodiments, the dichroic mirror reflects light of the wavelength emitted by light source 102. After being reflected off dichroic mirror 112, the light from light source 102 may travel along afferent light path 204 to the rotating mirror 110. Rotating mirror 110 may be offset from the central axis of the eye such that the light reflected off the rotating mirror 110 enters the eye from the periphery of the patient's field of view and produces a spot on the non-central location away from the fovea, for example on the patient's peripheral retina or the macula outside the fovea. Rotating mirror 110 may be offset from the central axis of the eye or otherwise angled such that the spot produced by light reflected off the rotating mirror 112 is offset from the patient's fovea at an angle within a range from 5° to 35°, preferably from 15° to 25°, for example at an angle of about 20° to the fovea. In some embodiments the angle may vary during measurement.

The rotating mirror 110 and the dichroic mirror 112 may rotate together. For example, the dichroic mirror and the rotating mirror may rotate about the same axis at the same rotational or angular speed with the dichroic mirror 112 reflecting light towards the rotating mirror 110. In some embodiments, the rotating mirror 110 and the dichroic mirror 112 rotate at a rate within a range from 5 RPM to 120 RPM, for example. In some embodiments, the rotating mirror 110 rotates in a stepwise fashion. For example, the rotating mirror 110 may rotate 5° and then stop in order to allow measurement of the spot formed on the non-central location of the retina outside the fovea, e.g. the peripheral retina or macula outside the fovea, and then rotate another 5° in order to allow measurement of the spot formed in the new position on the non-central location outside the fovea, e.g. on the peripheral retina or the macula outside the fovea. The rotating mirror may rotate in intervals between one degree and 120°. For example, in 1°, 5°, 10°, 15°, 30°, 45°, 60°, 90°, or 120° intervals. In this way, even as the rotating mirror 110 rotates about the axis, light from the dichroic mirror 112 is reflected towards the rotating mirror 110. As the rotating mirror 110 rotates about the central axis, the location of the spot formed on the patient's peripheral retina or macula outside the fovea similarly rotates about the patient's fovea. For example, afferent path 206 shows the path of light wherein the dichroic mirror 112 is in position 112A and rotating mirror 110 is in position 110A, both having rotated 180°. In this way, the refractive qualities of the patient's eye may be determined in a plurality of locations about the patient's retina.

In some embodiments, during operation of the system 100 during a second time period, light source 104 emits a beam of light along afferent path 204. The light beam travels along the afferent path 204 and is reflected off the beam splitter 106 and is then reflected off a surface of the beam splitter 108. The beam splitter 108 may be arranged such that light reflected off the beam splitter 106 is reflected off the beam splitting surface in a direction substantially parallel to the optical axis of the patient's eye. From the beam splitter 108, light from the light source 104 may be reflected off the dichroic mirror 112. In such embodiments, the dichroic mirror reflects light of the wavelength emitted by light source 104. After being reflected off dichroic mirror 112, the light from light source 102 may continue to travel along afferent light path 204 to the rotating mirror 110. Rotating mirror 110 may be offset from the central axis of the eye such that the light reflected off the rotating mirror 110 enters the eye from the periphery of the patient's field of view and produces a spot away from the fovea such as one or more of on the peripheral of the patient's retina or on an outer part of the patient's macula. Rotating mirror 112 may be offset from the central axis of the eye or otherwise angled such that the spot produced by light reflected off the rotating mirror 112 is offset from the patient's fovea.

As discussed above, the rotating mirror 110 and the dichroic mirror 112 may rotate together. For example, the dichroic mirror and the rotating mirror may rotate about the same axis at the same rotational or angular speed or in the same stepwise fashion with the dichroic mirror reflecting light towards the rotating mirror 110.

In some embodiments, from the beam splitter 108 the light continues along afferent light path 204 and may pass through the dichroic mirror 112. In such embodiments, the dichroic mirror allows light of the wavelength emitted by light source 104 to be transmitted therethrough. After passing through the dichroic mirror 112 the light continues to travel along afferent light path 202 through the patient's lens and cornea and into the patient's eye where it illuminates a spot on the fovea of the patient's retina 116. As discussed herein, dichroic mirror 112 may rotate about the central axis of the patient's eye or about the afferent light path 202. However, the rotation of the dichroic mirror may not affect the transmission of the light from light source 102 into the patient's eye and on to the fovea.

In the embodiment discussed above, light from light source 102 and light from light source 104 are emitted during different time intervals such that when light source 102 is emitting light, light source 104 is not emitting light and vice versa. In such embodiments the light from light source 102 and the light from light source 104 may be of the same wavelength. By alternating activation of the light sources 102, 104 the imager 120 may be able to separately image the spot formed on the fovea and the spot formed on the macula. In such embodiments, the dichroic mirror 112 may be replaced with a rotating prism or half mirror that transmits a portion of the incident light along afferent light path 202 while reflecting a portion of incident light along afferent path 204, for example.

In some embodiments, light source 102 and light source 104 may emit light during the same time period, e.g. at overlapping times or substantially simultaneously. In such embodiments, a dichroic mirror 112 may simultaneously allow passage of light from a first of the light sources 102, 104 of a first wavelength along afferent path 202 while reflecting light from a second of the light sources 102, 104 of a second wavelength along afferent path 204.

In some embodiments, a single light source that emits a plurality of wavelengths may be used. In such embodiments, the dichroic mirror 112 may transmit a first of the wavelengths emitted by the single light source along afferent path 202 onto the fovea while reflecting a second of the wavelengths emitted by the single light source along afferent path 204 onto the non-central location of the retina outside the fovea such as a peripheral retina location or a macula location outside the fovea. The image sensor 120 may comprise a first filter to selectively pass a first wavelength of the plurality of wavelengths onto first pixels of the imager and a second filter to selectively pass a second wavelength of the plurality of wavelengths onto second pixels of the plurality of pixels, in order to measure the plurality of wavelengths at overlapping times, e.g. simultaneously.

Figure 3:
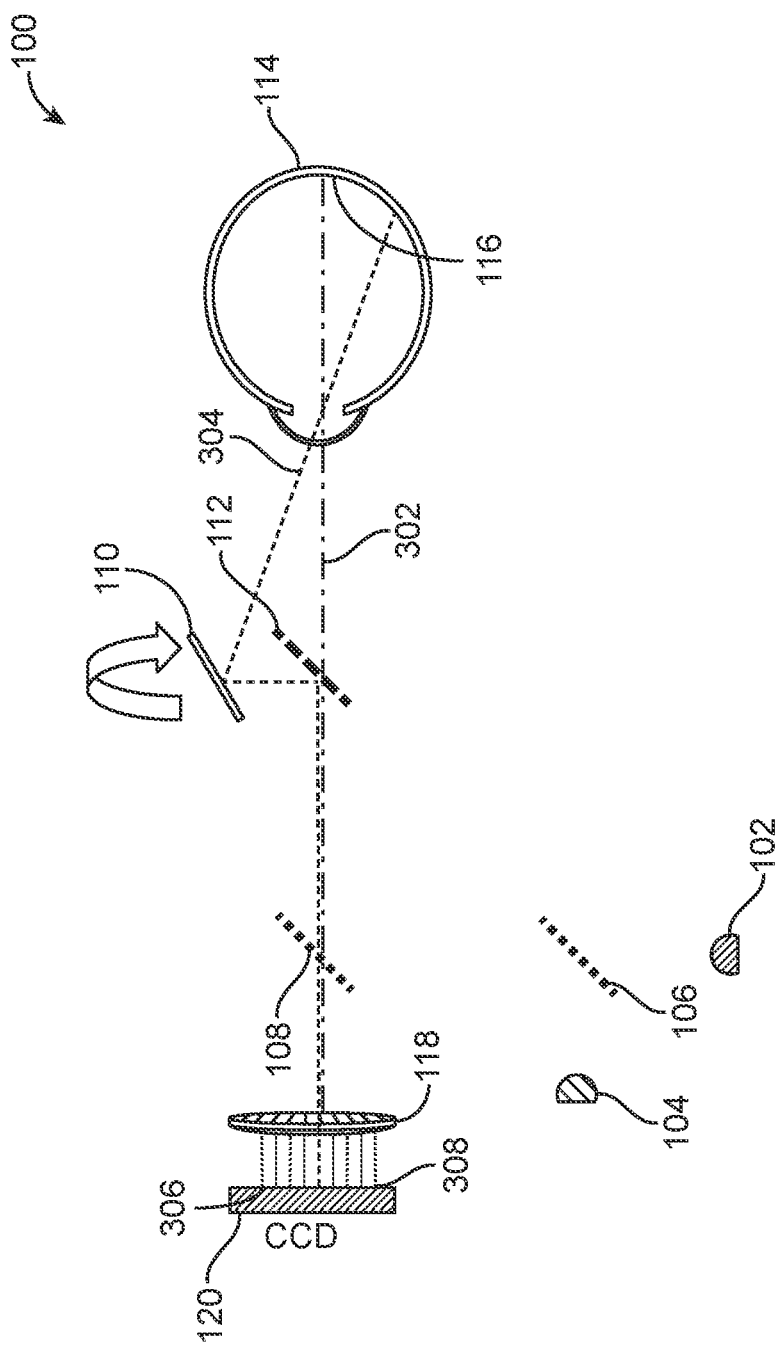
FIG. 3 shows a diagram of the efferent light path of the system of FIG. 1, in accordance with some embodiments.

FIG. 3 shows a diagram of the efferent light paths 302, 304 of the system of FIG. 1 for mapping the refractive error of the patient's eye. The efferent light paths 302, 304 are generated from locations of the retina illuminated with light travelling along afferent light paths 202, 204, respectively. During operation of the system 100, light from the peripheral of the retina 116 may travel along efferent path 304 to the rotating mirror 110. The light incident to the rotating mirror 110 is reflected off a reflective surface of the mirror 110 towards the dichroic mirror 112. In the embodiments shown in FIG. 3, the dichroic mirror 112 reflects the wavelength of light traveling along efferent path 304, which comprise similar wavelength to light travelling along efferent path 204, which is one or more of reflected or scattered from the illuminated location of the retina. The reflected light then passes through the beam splitter 108 and onto the micro lenslet array 118. The beam splitter 108 may comprise a partially reflective beam splitter or a polarizing beam splitter, for example. In some embodiments, the beam splitter 108 comprises a polarizing beam splitter and a circular polarizer is located between beam splitter 108 and mirror 112, for example.

Although depicted as a single light path, the efferent path 304 may include a plurality of light paths. While a single beam of light, such as a laser beam, may travel along afferent light paths 202, 204 to form respective spots on the central location comprising the fovea and the locations of the retina away from the fovea, the afferent light path may comprise a plurality of light paths originating at the respective spots at locations on the fovea and the locations of the retina away from the fovea, which travel along efferent paths 302, 304 to each of the plurality of lenslets in the micro lenslet array 118. The efferent path to each of the lenslets may be affected by the refractive properties of the patient's eye including the relative distance of the retina with respect to the lens and cornea of the patient and also the refractive properties of the lens and the cornea of the patient. In some embodiments, additional optical components such as a Badal optometer can be introduced along the common optical path of the afferent light paths 202, 204 and the efferent light paths 302, 304, so as to correct for refractive error of the eye.

The microlens array focuses each respective image of the respective spot onto the imaging device 120. The system 100 may be configured such that with an emmetropic eye the images of the spots formed on the image sensor 120 are located at positions corresponding to an emmetropic eye, such as known positions, whereas an eye with refractive errors or other anomalies may produce spots at different locations on the image sensor 120 as compared to the corresponding positions of the emmetropic eye.

The computing device 122 (omitted from FIGS. 2 and 3 for clarity) may determine the refractive errors of the patient's eye based on the deviations of the positions of the images of the spots on the image sensor. By imaging a spot on the fovea and spots at a plurality of locations on the peripheral of the retina such as about the macula, a refractive map of the patient's eye for different retinal locations may be determined. In some embodiments, the refractive map comprises a spherical optical power for each of the plurality of locations of the retina.

Figure 4:
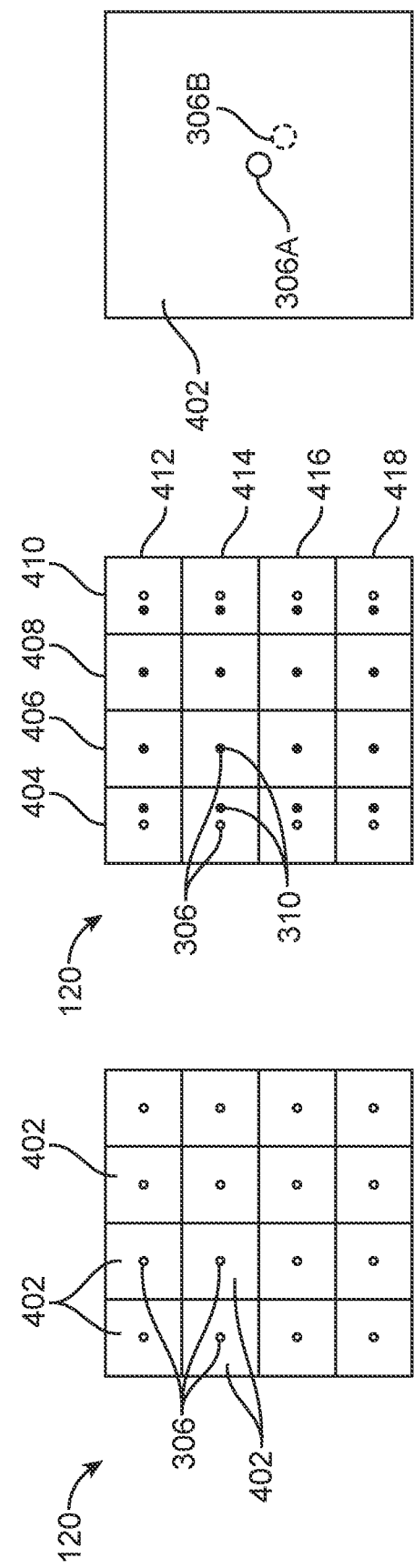
FIGS. 4A and 4B show the light projected on a sensor of the system of FIG. 1, in accordance with some embodiments.
FIG. 4C shows offset of a spot on an imaging area corresponding to refractive error, in accordance with some embodiments.

FIGS. 4A and 4B show the light projected on a sensor 120 of the system of FIG. 1. FIG. 4A shows the sensor 120 with the plurality of spots 306 formed on the sensor by a micro lenslet array 122 for one illumination of location of the afferent light beam on the retina, e.g. one light beam illuminating one location on the fovea or on a location of the retina away from the fovea such as the peripheral retina. As shown in FIG. 4A, each of the spots 306 is formed at a location on a corresponding imaging area of the plurality of imaging areas 402. In some embodiments, each of the spots is aligned with the center of each corresponding imaging area 402. In some embodiments, this shows that the imaged portion of the patient's eye is emmetropic for that location on the retina and has a substantially planar wavefront at that location. In some embodiments, the sensor 120 comprises a plurality of columns, such as columns 404, 406, 408 and 410, and a plurality of rows such as rows 412, 414, 416 and 418. In some embodiments, the location of a region is defined by the row and column of the region, and the location of the region corresponds to a location of the pupil. The mapping as described herein can be used to map the refractive error of the eye across the pupil for each location of the retina, in order to map the refractive data of the eye across the pupil for each retinal location.

FIG. 4C shows offset of a spot on an imaging area corresponding to refractive error. Location 306A shows a generally central location 306A of imaging area 402, in which spot 306B is formed at a location away from the location 306A corresponding to emmetropia. The locations of the plurality of spots 306 with reference to the center of each of the plurality of imaging areas 402 can be used to determine the optical properties of the eye at the corresponding location of the retina. For example, deviations of the spots 306 from central locations of corresponding areas 406 indicates one or more of a refractive error, a non-planar wavefront or aberrations of the eye. Although reference is made to spots 306 formed at the center of each of the plurality imaging areas, the location of the spots can vary and the computing device can be configured to identify locations of the spots 306 for each the plurality of areas 402 and determine one or more of the refractive error, wavefront, or aberrations of the eye in response to the locations of the spots 306 within the corresponding areas 402. Also, while reference is made to spots at center of each imaging area corresponding to emmetropia, in some embodiments the computing device can be calibrated to correct for offsets of the spots related to system alignment and other factors, such that the positions of the spots corresponding to emmetropia can be located away from the center of each area, as will be appreciated by one of ordinary skill in the art.

In some embodiments, the pupil of the eye is imaged onto the lenslet array, such that each of the plurality of imaging areas 402 corresponds to a region of the pupil. These locations of the spots 306 can be used to determine refractive data for the location of the retina illuminated with the light beam. The refractive data may comprise one or more sphere, cylinder, axis, aberrations, spherical aberration, coma trefoil, wavefront data, Zernike coefficients or wavefront maps for the illuminated location of the retina. For each of the plurality of locations on the retina, a similar spot pattern and refractive data can be generated, so as to provide refractive maps for each of the plurality of locations on the retina. Any appropriate refractive data as described herein can be mapped for each of the plurality of locations of the retina. For example, the root mean square (RMS) wavefront error of the eye can be mapped for each of the plurality of locations of the retina, as well as other refractive data as described herein.

The image sensor 120 shown in FIG. 4A includes a plurality of imaging areas 402, e.g. 16 imaging areas in a 4 by 4 square array. In such embodiments, a corresponding micro lenslet array may include 16 micro lenses or lenslets in a similar 4 by 4 square array. Each imaging area 402 may comprise a plurality of pixels. Although reference is made to a 4×4 array, any suitably sized array can be used, and the array may comprise non-rectangular shapes.

The image shown in FIG. 4A may correspond to the operation of system 100 wherein only a single light source is operated during a particular time period and accordingly only a single spot on the patient's retina is imaged by the imaging sensor 120.

The image shown in FIG. 4B may correspond to the operation of system 100 wherein a plurality of beams comprising wavelengths, such as from a single broadband light source or from a plurality of light sources that emit different wavelengths, are projected onto the retina of the patient during a particular time period and accordingly two spots spot on the patient's retina are imaged by the imaging sensor 120. This figure also illustrates how the refractive data, e.g. refraction, of the eye can change for different locations of the retina. The first spots 306 may correspond to images of a spot projected onto the fovea of the patient's eye while the second spots 310 may correspond to images of a spot projected away from the fovea such as onto the peripheral retina or areas of the macula away from the fovea of the patient's eye. As shown in FIG. 4B, images of the spots 310 in columns 404 and 410 of the image sensor 120 are displaced from the center of the respective imaging areas and also displaced from the spots 306 corresponding to light projected onto the fovea. As described herein, each of the regions 402 may correspond to a region of the pupil. Accordingly, this offset of the spots shows that there are refractive errors corresponding to the locations of the spots on the patient's retina and corresponding wavefront errors for the corresponding locations of the pupil of the eye. In columns 406 and 408 the spots 306 from light projected on the fovea of the patient overlap with the spots 310 from light projected onto the retina at locations away the fovea such as the locations of the macula away from the fovea and the peripheral retina of the patient. The overlap of the spots indicates that the refractive properties of the eye are similar for the foveal measurement light beam and the non-foveal measurement light beam for the locations of the pupil corresponding to columns 406 and 408 on the sensor 120.

For each retinal location, refractive data across the pupil can be determined and processed accordingly. For example, for each retinal location a wavefront map across the pupil can be generated. Alternatively or in combination, the refractive data can be processed to generate a refraction of the eye for each retinal location. In some embodiments, the refractive error for each retinal location is used to generate a map of refractive error for the retinal locations. The mapped refractive error may comprise a map of spherical equivalent refractive error across the retina, a map of sphere across the retina, or a map of cylinder across the retina. Similar maps can be generated with respect to other types of refractive data as described herein, such as a map of spherical aberration across the retina, a map of coma across the retina, or a map of trefoil across the retina. In some embodiments Zernike coefficients are used to generate maps of aberrations across the retina. As one of ordinary skill in the art will appreciate, the lower order Zernike coefficients correspond to prism, sphere and cylinder, and the higher order Zernike coefficients correspond to aberrations such as spherical aberration and trefoil. In some embodiments, a map across the retina is generated for each of a plurality Zernike coefficients. For example, the Zernike coefficient for the measured area of the pupil can be determined for first measurement beam location on the retina, the Zernike coefficient determined for a second measurement location on the retina, up to a total number of measurement locations on the retina, and map of the Zernike coefficients for the measured locations generated. This process can be repeated for additional Zernike coefficients.

In some embodiments, the spots 306 and 310 may be of different wavelengths. In order to simultaneously image spots of different wavelengths the plurality of pixels within each imaging area 402 may have a corresponding filter as described herein, for example. Alternatively, the different locations can be sequentially imaged as described herein.

In a sensor designed to image two or more different wavelengths, the array may have alternating filters such that every other pixel within the array receives light of a first wavelength while neighboring pixels receive light of a second wavelength. In some embodiments the system may include two or more filters that are selectively placed in front of the image sensor 120. In some embodiments, the illumination and imaging of different wavelengths is performed simultaneously. Alternatively or in combination, light of a first wavelength may be imaged during first time period while light of a second wavelength is imaged at a second time period.

Although FIGS. 1 to 4C refer to system 100 comprising a lenslet array such as a lenslet array of a Hartman Shack wavefront sensor, system 100 can be configured in many alternative ways without a lenslet array. In some embodiments, one or more of the afferent light paths 202, 204 or 206 comprises light of an optical coherence tomography ("OCT") measurement beam, such as a swept source OCT measurement beam, and one or more of efferent light paths 302, 304, 306 comprises OCT light from the retina at locations as described herein, and the OCT measurement beam is used to measure an axial length of the eye. In some embodiments, one or more of light source 102 or light source 104 comprises an OCT light source used to generate the corresponding afferent beam, and the one or more of light sources 102 or light source 104 is configured to transmit light to the fovea and locations of the retina away from the fovea as described herein. The detector and lenslet array can be replaced with OCT measurement components coupled to computing device 122 to map the refractive error of the eye at a plurality of locations as described herein, which components will be understood by one of ordinary skill in the art in accordance with the teachings of the present disclosure. In some embodiments, the system 100 comprises a scanning slit autorefractor, in which the scanning slit auto refractor is configured to measure the refraction of the eye to the fovea and to locations of the eye away from the fovea, as described herein. For example, one or more of light source 102 or light source 104 comprises a light source of a scanning slit autorefractor to provide afferent measurement beams along afferent light paths 202, 204, 206, and the detector coupled to the computing device 122 is configured to measure afferent light along afferent light paths 302, 304, 306, in order to map the refractive error of the eye at a plurality of retinal locations as described herein. The system 100 can be configured with suitable optical, mechanical and electrical components to measure the refractive data of the eye as described herein, as will be understood by one of ordinary skill in the art.

Figure 5:
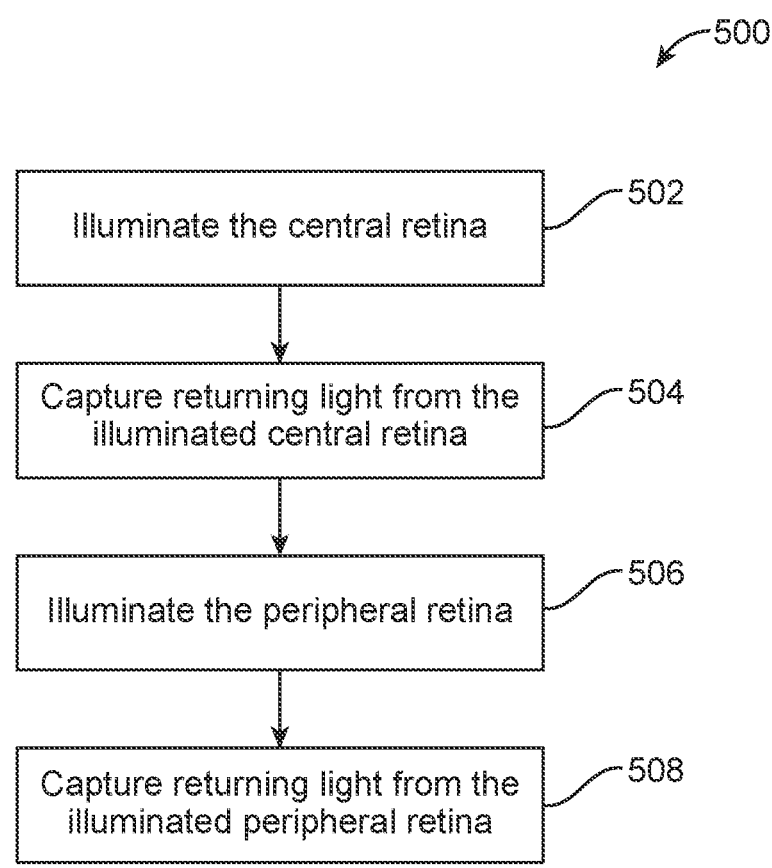
FIG. 5 shows a method of mapping the central and non-central retina, such as the foveal and non-foveal regions of the retina, in accordance with some embodiments.

FIG. 5 shows a method 500 of mapping the fovea and locations of the retina away from the fovea such as the macula outside the fovea and the peripheral retina. At step 502 the central retina or fovea is illuminated. In system 100, instructions stored in memory on the computing device 120 may be executed by the processor in order to cause a signal to be sent to the first light source 102 in order to turn on the first light source 102. Light emitted from the first light source 102 may be projected through one or more optical elements, as described above with respect to FIGS. 1 to 3, in order to form a spot on the central retina or fovea of the patient.

At step 504 efferent light 302 from the spot projected on the central retina or fovea of the patient is projected through one or more optical elements including a micro lenslet array 118, as described above with respect to FIGS. 1 to 3. Light from the microlens 118 is projected onto in imaging device such as imaging device 120. Instructions stored in memory on the computing device 122 may be executed by the processor which may send a signal to the imaging device 122 to cause the imaging device 122 to record the images projected thereon during the illumination of the first light source.

At step 506 the retina is illuminated at a location outside the fovea, such as a location of the macula outside the fovea or a location of the peripheral retina. In system 100, instructions stored in memory on the computing device 120 may be executed by the processor in order to cause a signal to be sent to the first light source 102 in order to turn on the second light source 104. Light emitted from the first light source 104 may be projected through one or more optical elements, as described above with respect to FIGS. 1 to 3, in order to form a spot at a first location on the retina away from the fovea such as the peripheral retina or a location of the macula outside the fovea.

At step 508, efferent light 304 from the spot projected on the location of the retina away from the fovea such as the peripheral retina or macula away from the fovea is projected through one or more optical elements including a micro lenslet array 118, as described above with respect to FIGS. 1 to 3. Light from the microlens 118 is projected onto an imaging device such as imaging device 120. Instructions stored in memory on the computing device 122 may be executed by the processor which may send a signal to the imaging device 122 to cause the imaging device 122 to record the images projected thereon during the illumination of the second light source.

In some embodiments, after steps 506 and 508, the computing device may cause the rotating mirror 110 to rotate an incremental amount, such as a predetermined distance about the central axis of the patient's eye. After which steps 506 and 508 may be repeated. Such rotation may cause the location of the spot to rotate to a second location away from the fovea such as a location on the peripheral retina or macula of the patient's eye. This sequential rotation, illumination, and capturing may be repeated in order to image the periphery of the patient's eye. For example, steps 506 and 508 may be repeated 24 times at 15° increments in order to image a 360° circle about the periphery of the patient's retina.

In some embodiments steps 506 and 508 may additionally be repeated at various peripheral offsets from the patient's fovea for example the patient's eye may be image in a 360° circle at a 10° offset from the patient's fovea and then again in a 360° circle at a 20° offset from the patient's fovea.

In some embodiments, each of steps 502, 504, 506, 508 may occur at the substantially the same time, e.g. at overlapping times or substantially simultaneously. For example, when illuminating the central retina, e.g. the fovea, with a first wavelength of light from a first light source while simultaneously illuminating the retina way from the fovea, e.g. peripheral retina or macula, with a second light source of a second wavelength a color or filtered imaging device may capture both wavelengths at the same time. In some embodiments, steps 502, 504, 506, 508 may occur sequentially as shown in FIG. 5.

Although FIG. 5 shows a method mapping refractive error of the central retina, e.g. the fovea, and the peripheral retina or macula away from the fovea in accordance with some embodiments, a person of ordinary skill in the art will recognize many adaptations and variations. For example, some of the steps can be repeated, some of the steps can be omitted, and the steps can be performed in any suitable order.

Figure 6:
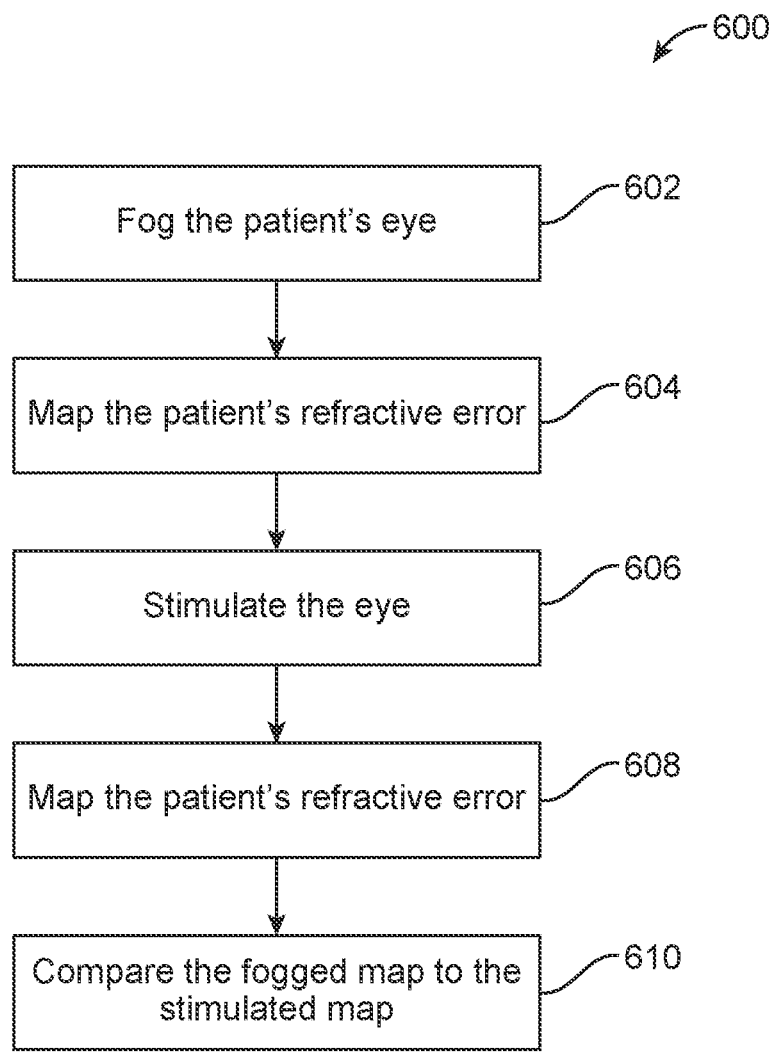
FIG. 6 shows a method of diagnosing a patient using the systems and methods described herein, in accordance with some embodiments.

FIG. 6 shows a method 600 that may be used to predict, diagnose, plan and monitor a patient. At step 602 the patient's eye is fogged in order to cause the patient to relax the focus of their eye. In some embodiments fogging the patient's eye causes the patient to relax the accommodation of their eye to focus the eye at a far point, for example, optical infinity. With the eye fogged, at step 604 the patient's refractive error is mapped. Mapping the patient's refractive error may include carrying out the steps of method 500 in order to image the central retina and the non-central retina, e.g. the peripheral retina, and then, based on those images, determine a refractive map of the patient's central retina and non-central retina such as the peripheral retina and the macula away from the fovea.

At step 606 the patient's eye may be stimulated. For example, the patient's eye may be stimulated with a near stimulus in order to cause the patient to attempt to focus their eye. For example, the patient may be stimulated with a 2 D stimulus to cause them to attempt to focus their eye to accommodate the stimulus. With the eye stimulated, at step 608 the patient's refractive error is mapped. Mapping the patient's refractive error may include carrying out the steps of method 500 in order to image one or more of the central retina, e.g. the fovea, the macula or peripheral retina of the patient and then based on those images determine a refractive map of the patient's central retina and non-central locations such as the macula away from the fovea and peripheral locations of the retina during stimulation.

At step 610 the refractive map of the eye measured during fogging may be compared to the refractive map of the eye measured during accommodative stimulation and, based on these refractive maps, a prediction, diagnosis, or plan may be made. For example, during stimulation children may fail to accommodate the full 2 D of stimulation. Instead, their accommodation may lag for example by 1 D. Such a lag of accommodation may be related to, e.g. predictive, of future myopia of the patient. If a lag is detected, treatment may be prescribed to the patient in order to delay, prevent, or reduce the onset of myopia.

In some embodiments, the refractive map of the patient's eye may be used to diagnose refractive errors of the patient's eye, abnormalities in the shape of the patient's retina, or other conditions of the patient's eye.

In some embodiments, patients may have a different lag of accommodation in the central retina as compared to non-central locations of the retina such as the peripheral retina and locations of the retina away from the fovea. Knowledge of such lag of accommodation lead a health care professional such as doctor to prescribe treatment to correct the peripheral lag of accommodation.

In some embodiments, the refractive map may be used in order to aid in the treatment and prevention of the patient's myopia. For example, the use of defocused images on the patient's retina may cause stimulation of one or more of the patient's choroid or sclera related to changes in the length of the patient's eye. Such stimulation may one or more of decrease, prevent or reverse the onset of myopia. The defocused images may be projected from the periphery of the patient's vision onto areas of the retina other than the fovea patient's eye. By using the map the refractive properties of the patient's eye about the periphery of the patient's retina, a healthcare professional such as a doctor may adjust the defocus of the stimulation in order to account for differences in the refractive properties associated with the central retina, e.g. the fovea and areas of the retina away from the fovea such as the peripheral retina and macula away from the fovea.

In some embodiments, the steps of FIG. 6 may be repeated over time in order to monitor a patient's progress or lack thereof with a given treatment. Based on the changes in the refractive map of the patient (or lack thereof) a doctor may alter the patient's treatment. For example, if a patient's progress is slower than expected a doctor may prescribe additional or greater stimulation in order to increase the effectiveness of the treatment. Conversely if a patient's treatment is progressing faster than expected a doctor may in treatment early or adjust the patient's stimulation in order to account for the patient's faster than expected progress.

The systems as described herein can be configured in many ways to measure the retina with light. In some embodiments, the light emitted by the first light source comprises a first band wavelengths and the light emitted by the second light source comprises a second a band of wavelengths, the second band wavelengths at least partially overlapping with the first band of wavelengths. In some embodiments, the first light source is configured to emit the first band of wavelengths at a first time and the second light source is configured to emit the second band of wavelengths at a second time different from the first time.

The axial length can be measured in many ways. In some embodiments, the axial length comprises a relative change in axial length between the central location of the retina and the peripheral location of the retina. In some embodiments, the processor is configured with instructions to determine the change in axial length in response to a change in the refractive properties of the eye between the central location of the retina and the peripheral location of the retina. In some embodiments, an axial length change of approximately 1 mm corresponds to a change in axial length of approximately 3 Diopters ("D") and this change in refractive properties can be used to determine the change in axial length. For example, a change in refraction of −1 D corresponds to an increase in axial length of approximately ⅓ mm. In some embodiments, the processor is configured with instructions to determine the change in axial length in response to difference between an axial length measured at the central location of the retina with an OCT measurement beam and the axial length measured at the peripheral location of the retina measured with the OCT beam.

Figure 7:
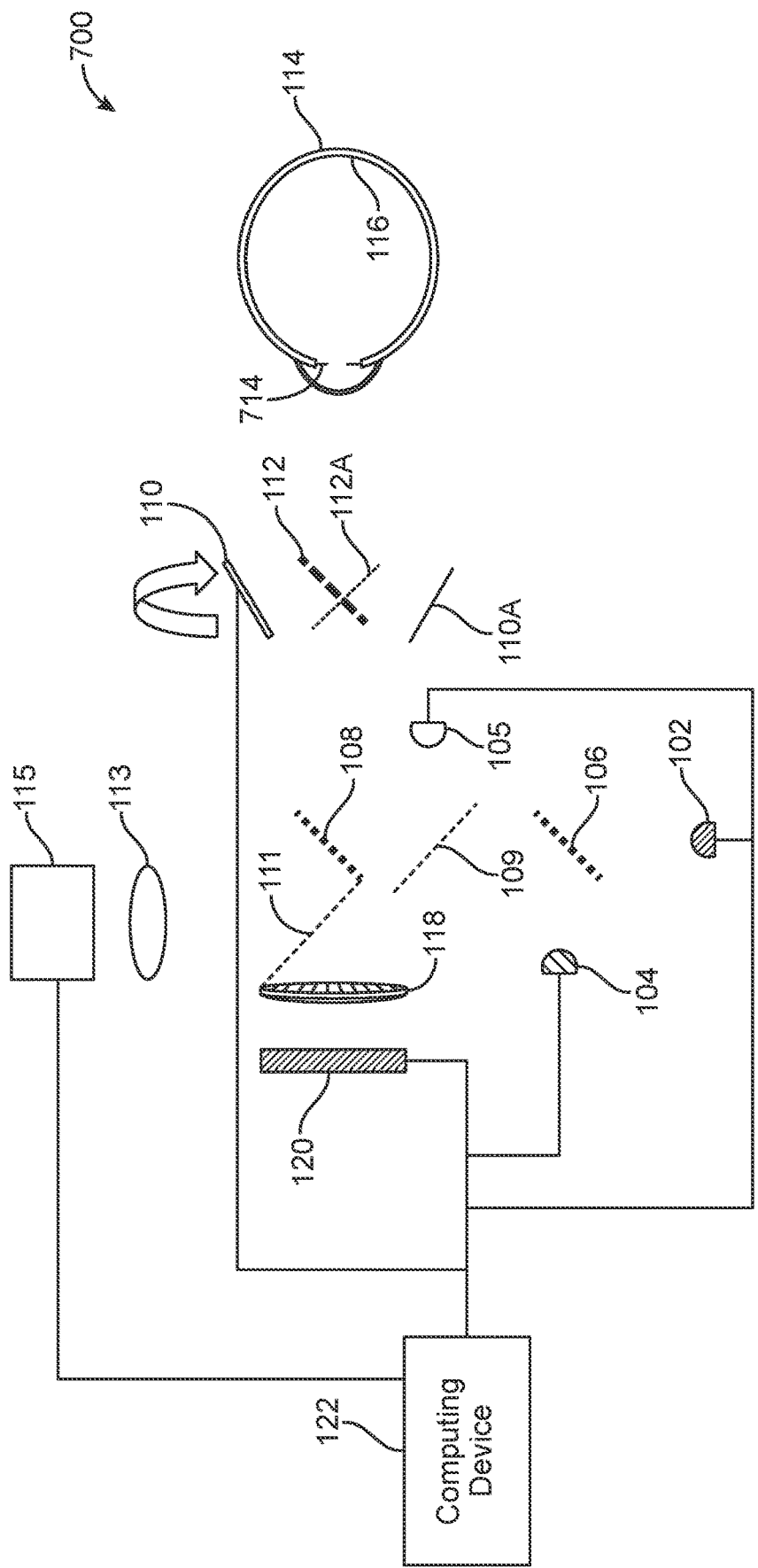
FIG. 7 shows a system to map the refractive error the eye at a central retina location, e.g. the fovea, and a non-central location of the retina, e.g. the peripheral retina or macular location outside the fovea, in which the system comprises a stimulus and a pupil camera, in accordance with some embodiments.

FIG. 7 shows a system 700 to map the refractive error the eye at central and peripheral locations of the retina, in which the system comprises a stimulus and a pupil camera. The system 700 may comprise one or more components of system 100 as described herein. In some embodiments the system 700 comprises a stimulus 105 coupled to the computing device 122, and a reflective component 109, such as a mirror or beam splitter as described herein to present the stimulus to the eye. In some embodiments, the system 700 comprises an optical component 113 and a sensor array 115 coupled to the computing device 122 to measure a location of the pupil 714 of the eye. In some embodiments, the optical component 113 and sensor array 115 are coupled along the afferent and efferent optical paths with a reflective component 111 such as a mirror or beam splitter as described herein. The optical component 113 may comprise one or more lenses to form an image of the pupil on the sensor array. In some embodiments, the sensor array 115 and the optical component 113 comprise components of a pupil camera.

In some embodiments, the stimulus 105 comprises one or more lenses to adjust the vergence of the stimulus in Diopters as presented to the eye, such as for a near vision presentation or a far vision presentation of the stimulus. Alternatively or in combination, the stimulus may comprise one or more components such as a lenses or prisms or a display to adjust the lateral position of the eye to correspond with the apparent distance of the eye from the stimulus.

Figure 8:
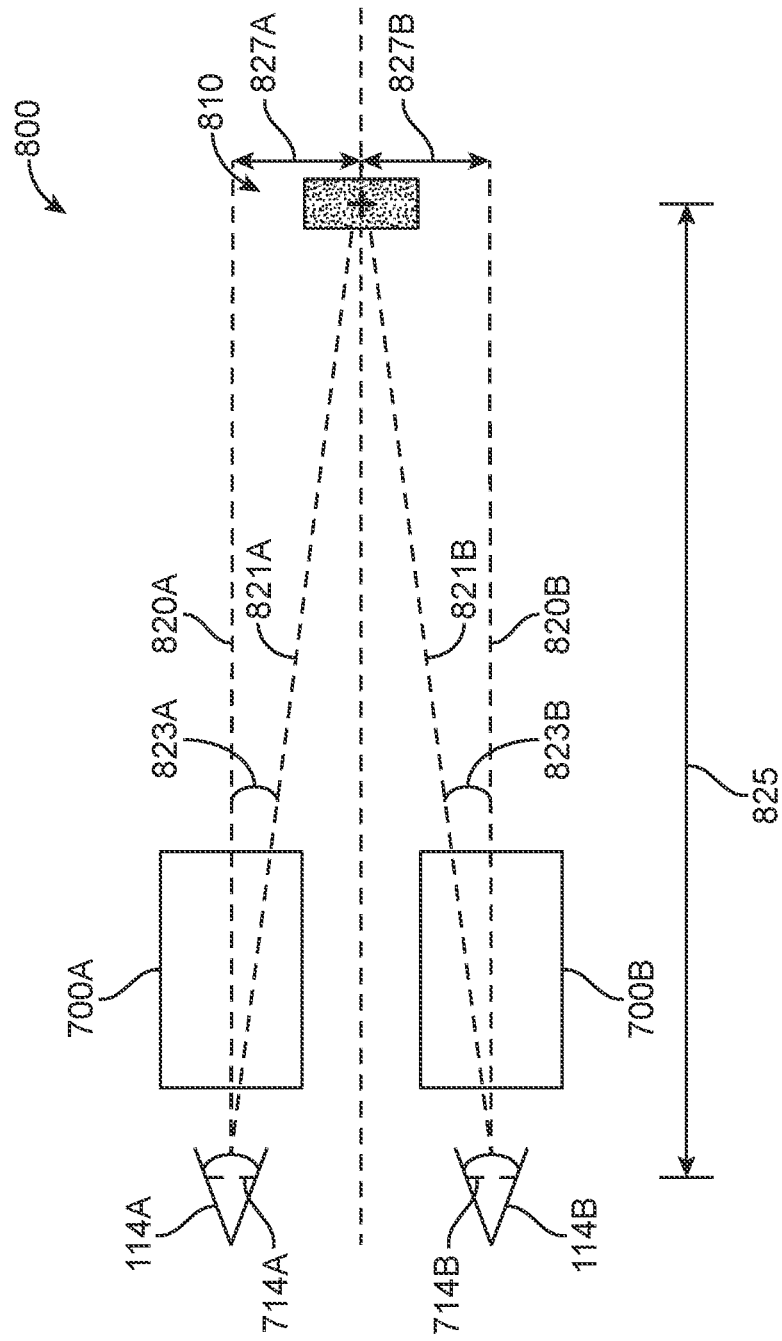
FIG. 8 shows a system to map refractive error of eyes at central locations and non-central locations of the retina with a binocular stimulus, in accordance with some embodiments.

FIG. 8 shows a system 800 to map refractive error of eyes at central and peripheral locations of the retinas with a binocular stimulus 810. The system may comprise a system 700A to measure components of an eye 114A of the patient and a system 700B to measure the fellow eye 114B of the patient. Each of system 700A and the system 700B may comprise on or more components of the system 700 as described herein. In a near vision configuration of the binocular stimulus 810, the line of sight 821A of the eye is directed toward the binocular stimulus, and the line of sight 821B of the fellow eye is directed to the binocular stimulus 810. In eyes with appropriate vergence toward the stimulus, the vergence angle 823A of the eye and the vergence angle 823B of the fellow eye correspond to the distances from the eyes to the stimulus and the offset angle between each eye and the stimulus. When the binocular stimulus is in a far vision configuration, e.g. corresponding to an infinite distance from the eye 114A and fellow eye 114B, the eye 114A views the binocular stimulus 810 along line of sight 820A and the eye 114B views the binocular stimulus 810 along the line of sight 820B.

In some embodiments, the lateral location of the stimulus 105 is adjusted in each of system 700A and system 700B, so as to correspond with the lateral offsets 827A, 827B, respectively, and distance 825 of binocular stimulus 800. In some embodiments, the stimulus is located at a distance of 2 meters or more to correspond to far vision (vergence of 0.5 Diopter or less) and located at a distance of 1 meter or less (vergence of 1.0 D or more) so as to correspond to a near vision. The stimulus may comprise one or more of a physical object, a real image or a virtual image.

In some embodiments, the pupil camera of each of system 700A and system 700B is configured to measure a position of the pupil of each eye in the near vision configuration and the far vision configuration in order to determine the vergence of the eyes. In some instances, the lines of sight of the eyes may not converge to the target in the near vision configuration, which may indicate that the patient does not have appropriate vergence and this can be used for diagnostic purposes and treatment planning as described herein. For example, the position of the pupil of each eye can be measured in the far vision configuration, and the pupil of each eye measured in the near vision configuration. The offsets of the pupils between the near vision configuration of the far vision configuration can be used to measure the vergence angle of each eye. The vergence angle of the eyes can be compared to angles 823A and 823B. This comparison can be used to determine if the vergence of the eyes lags the vergence of the stimulus based on the vergence angles of the eyes and the angles 823A and 823B of the stimulus.

In some embodiments, one or more components of system 700A or system 700B is adjustable to correspond to the inter pupillary distance ("IPD") of the eye 114A and the fellow eye 114B. For example, one or more of the systems 114A or system 114B can be mounted on a translation stage to adjust to the IPD. Alternatively or in combination one or more optical components can be adjusted to compensate for the IPD.

In some embodiments, a first detector array is configured to measure a first pupil of a first eye and a second detector array is configured to measure a second pupil of a second eye in response to the stimulus, and the processor is configured with instructions to measure a first distance between the first pupil and the second pupil in response to a first stimulus and a second distance between the first pupil and the second pupil in response to a second stimulus to determine ocular vergence of the first eye and the second eye in response to the first stimulus and the second stimulus.

In some embodiments, a light source and stimulus optics to provide a binocular stimulus to the eye and a second eye of the patient, the light source and stimulus optics configured to present the binocular stimulus at an apparent distance and apparent angle between the first eye and the second eye corresponding to a near object.

The system can be configured in many ways to measure vergence of the eye with the binocular stimulus. In some embodiments, the stimulus is presented binocularly as described herein, and the system changed from a first eye configuration to measure a first eye to second configuration to measure the second eye. In some embodiments, the refractive properties of the eye, e.g. refractive data, is measured with the afferent and efferent beams as described herein, aligned with a first eye, and the first eye measured, and the system rotated to measure the refractive properties of the second eye sequentially. In some embodiments, the system comprises optics to present the binocular stimulus to the eye and the fellow eye while the eye is measured, and then a mirror or other component adjusted to measure the second eye and present the stimulus to the first eye. In some embodiments, the system comprises a nose bridge or other structure to couple to the patient for measurement of the first eye, and then the optics and measurement system are repositioned to measure the second eye.

In some embodiments, a detector array to measure one or more of a size or a location of a pupil in response to a stimulus presented to a pupil. In some embodiments, the processor is configured with instructions to measure a first pupil of a first eye and a second pupil of a second eye and to determine an ocular vergence of the first eye and the second eye in response to the stimulus.

In some embodiments, the processor is configured with instructions to measure a first distance between the first pupil and the second pupil in response to a first stimulus and a second distance between the first pupil and the second pupil in response to a second stimulus to determine ocular vergence of the first eye and the second eye in response to the first stimulus and the second stimulus.

In some embodiments, the detector array is configured to move from a first position to measure a first position from the first pupil and to a second position to measure a second position from the second pupil.

The system can be configured in many ways to operate with remote digital devices, such as a remote server, e.g. a cloud based server, as will be appreciated by one of ordinary skill in the art. In some embodiments, the processor is configured with instructions to transmit the refractive properties of the eye, e.g. refractive data as described herein, to a remote server. In some embodiments the data transmitted to the remote server comprises data for the central location and the peripheral location as described herein. In some embodiments, the processor is configured to transmit a map of refractive data of the eye to the remote server. The remote server configured to receive and store the refractive properties of the eye and to transmit the refractive properties to a mobile computing device of remote user, such as a health care professional or a family member. The mobile computing device may comprise any suitable device such as a smart phone, a tablet, a notebook computer, or desktop computer. The refractive data as described herein can be used by the remote user for analysis, diagnosis and treatment planning for example.

As described herein, the processor or computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the apparatuses or devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively, or in combination, the processor can be configured to combine one or more steps of one or more methods as disclosed herein. The processor as disclosed herein can be configured with instructions to perform any one or more steps of any method as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. An apparatus to measure relative refractive properties of an eye, comprising: one or more light sources configured to emit light; projection optics arranged to project the light emitted by the one or more light sources onto a foveal location of the retina and a non-foveal location of the retina; imaging optics arranged to generate a plurality of images from the light projected onto the foveal location of the retina and the non-foveal location of the retina; an imaging device configured to capture the plurality of images from the efferent optics; and a processor coupled to the imaging device, the processor configured to determine refractive properties of the eye for the foveal location of the retina and the non-foveal location of the retina.

Clause 2. The apparatus of clause 1, wherein the eye comprises a pupil and wherein light to the foveal location of the retina travels through the pupil at a first angle and light to the non-foveal location of the retina travels through the pupil at a second angle different from the first angle and wherein the refractive properties of the eye for the foveal location of the retina correspond to light traveling to the foveal location through the pupil at the first angle and the refractive properties of the eye for the non-foveal location of the retina correspond to light traveling through the pupil at the second angle.

Clause 3. The apparatus of clause 1, wherein the imaging optics comprise one or more of a lens or a lenslet array and wherein the plurality of images comprises one or more of a plurality images of a slit or a plurality of images of spot pattern.

Clause 4. The apparatus of clause 1, wherein the refractive properties of the eye for the foveal location of the retina comprise one or more of a first sphere, a first cylinder, a first axis, a first spherical equivalent, first coefficients of a wavefront map or a first wavefront map and the refractive properties of the eye for the non-foveal location of the retina comprise one or more of a second sphere, a second cylinder, a second axis, a second spherical equivalent, second coefficients of a second wavefront map or a second wavefront map.

Clause 5. The apparatus of clause 1, wherein the processor comprises instructions to generate a refractive map of the eye based on the plurality of images captured by the imaging device, the refractive map comprising first refractive properties corresponding to the foveal location of the retina and second refractive properties corresponding to the non-foveal location of the retina.

Clause 6. The apparatus of clause 1, wherein the one or more light sources and the projection optics are arranged to project the light emitted by the one or more light sources into the eye along a first afferent light path to the foveal location of the retina and a second afferent light path to the non-foveal location of the retina.

Clause 7. The apparatus of clause 6, wherein the foveal location of the retina comprises a fovea within a macula of the central retina and wherein the non-foveal location of the retina comprises a location of the retina outside the macula.

Clause 8. The apparatus of clause 7, wherein the second afferent light path is arranged at an angle of at least 10 degrees from the angle of the first afferent light path.

Clause 9. The apparatus of clause 7, wherein light from a first of the one or more light sources is projected along the first afferent light path and light from a second of the one or more light sources is projected along the second afferent light path.

Clause 10. The apparatus of clause 9, wherein the light emitted by the first light source comprises a first wavelength and the light emitted by the second light source comprises a second, different wavelength.

Clause 11. The apparatus of clause 10, wherein the first wavelength and the second wavelength comprise wavelengths in the near-infrared spectrum.

Clause 12. The apparatus of clause 10, wherein the first wavelength and the second wavelengths are at separated by at least 10 nm and optionally by at least 50 nm.

Clause 13. The apparats of clause 8, wherein the first afferent light path enters the eye along a central axis of the eye and the second afferent light path enters the eye at an angle to the central axis of the eye.

Clause 14. The apparatus of clause 1, wherein the imaging optics comprise a lenslet array.

Clause 15. The apparatus of clause 14, wherein lenslet array comprises a two-dimensional array.

Clause 16. The apparatus of clause 1, wherein the lenslet array comprises a plurality of one or more of round lenslets, gradient index lenslets, diffractive lenslets or crossed cylindrical rods.

Clause 17. The apparatus of clause 1, wherein the imaging optics are arranged between the imaging device and the patient's eye.

Clause 18. The apparatus of clause 1, wherein the imaging device comprises one or more of a CCD or CMOS imaging sensor.

Clause 19. The apparatus of clause 10, wherein the imaging device is configured to separately capture the first wavelength of light and the second wavelength of light.

Clause 20. The apparatus of clause 1, wherein the imaging device comprise a first set of pixels sensitive to the first wavelength of light and a second set of pixels sensitive to the second wavelength of light.

Clause 21. The apparatus of clause 20, wherein the light projected onto the first set of pixels is filtered to exclude light of the first wavelength and the light projected onto the second set of pixels is filtered to exclude light of the second wavelength.

Clause 22. The apparatus of clause 9, wherein the light emitted by the first light source comprises a first band wavelengths and the light emitted by the second light source comprises a second a band of wavelengths, the second band wavelengths at least partially overlapping with the first band of wavelengths.

Clause 23. The apparatus of clause 22, wherein the first light source is configured to emit the first band of wavelengths at a first time and the second light source is configured to emit the second band of wavelengths at a second time different from the first time.

Clause 24. The apparatus of clause 1, wherein the projection optics and the imaging optics comprise one or more common optical elements.

Clause 25. The apparatus of clause 1, wherein the processor is further configured to determine the axial length of the eye, based on the images.

Clause 26. The apparatus of clause 25, wherein the axial length comprises a relative change in axial length between the foveal location of the retina and the non-foveal location of the retina.

Clause 27. The apparatus of clause 26, wherein the processor is configured with instructions to determine the change in axial length in response to a change in the refractive properties of the eye between the foveal location of the retina and the non-foveal location of the retina.

Clause 28. The apparatus of clause 26, wherein the processor is configured with instructions to determine the change in axial length in response to difference between an axial length measured at the foveal location of the retina with an OCT measurement beam and the axial length measured at the non-foveal location of the retina measured with the OCT beam.

Clause 29. The apparatus of clause 25, wherein the processor is further configured to determine the axial length of the eye at the fovea and over a range of eccentricates of up to 6 degrees from the fovea.

Clause 30. The apparatus of clause 1, wherein the one or more light sources, the projection optics, the imaging optics, the imaging device and the processor are configured to determine the refractive properties of the eye with a measurement beam selected from the group consisting of a OCT measurement beam, a wavefront measurement beam and a scanning slit measurement beam.

Clause 31. The apparatus of clause 30, wherein the measurement beam comprises the OCT measurement beam and wherein the one or more light sources comprises a swept source to sweep wavelengths of the measurement beam, the projection optics comprise one or more optics to focus the measurement beam on the retina, the imaging optics comprise optics to image efferent light from the retina onto the imaging device, the imaging device comprises a detector to measure interference frequencies of light from the retina, and the processor is configured to measure a distance from a reference structure to the retina at each of the foveal location of the retina and the non-foveal location of the retina to determine the axial length of the eye at the foveal location and the non-foveal location.

Clause 32. The apparatus of clause 31, wherein the reference structure comprises one or more of a cornea of the eye, a lens of the eye or a reference structure of an OCT measurement system and optionally wherein the reference structure of the OCT measurement system comprises one or more of a mirror, an optical fiber or a coupler of the OCT measurement system.

Clause 33. The apparatus of clause 31, wherein the plurality of images comprises an A-scan of the OCT measurement beam at the fovea location and an A-scan of the OCT measurement beam at the non-foveal location.

Clause 34. The apparatus of clause 30, wherein the measurement beam comprises the wavefront measurement beam, the projection optics comprise one or more optics to focus the measurement beam onto the retina, the imaging optics comprise a plurality of lenslets to image efferent light from the retina onto the imaging device with a plurality of spots, the imaging device comprises an array detector to measure locations of each of the plurality of spots on the detector array, and the processor is configured to determine refractive data of the eye at the foveal location and the non-foveal location.

Clause 35. The apparatus of clause 30, wherein the measurement beam comprises the scanning slit measurement beam, the projection optics comprise one or more optics to image a scanning slit of the measurement beam onto the retina, the imaging optics comprise one more lenses to image the scanning slit onto the imaging device, the imaging device comprises a detector to measure the slit, and the processor is configured to determine refractive data of the eye at the foveal location and the non-foveal location.

Clause 36. The apparatus of clause 1, further comprising a stimulus to stimulate an accommodative response of the eye and one or more optics to adjust a vergence of the stimulus to stimulate the accommodative response.

Clause 37. The apparatus of clause 36, wherein the projection optics are configured to adjust the vergence of the stimulus.

Clause 38. The apparatus of clause 37 wherein the imaging optics are configured to adjust with the projection optics.

Clause 39. The apparatus of clause 38, wherein the projection optics and the imaging optics comprise one or more common optics and along a common optical path of afferent light to the retina and efferent light from the retina.

Clause 40. The apparatus of clause 1, further comprising a detector array to measure one or more of a size or a location of a pupil in response to a stimulus presented to a pupil.

Clause 41. The apparatus of clause 40, wherein the processor is configured with instructions to measure a first pupil of a first eye and a second pupil of a second eye and to determine an ocular vergence of the first eye and the second eye in response to the stimulus.

Clause 42. The apparatus of clause 41, wherein the detector array is configured to move from a first position to measure a first position from the first pupil and to a second position to measure a second position from the second pupil.

Clause 43. The apparatus of clause 40, further comprising a first detector array to measure a first pupil of a first eye and a second detector array to measure a second pupil of a second eye in response to the stimulus, and wherein the processor is configured with instructions to measure a first distance between the first pupil and the second pupil in response to a first stimulus and a second distance between the first pupil and the second pupil in response to a second stimulus to determine ocular vergence of the first eye and the second eye in response to the first stimulus and the second stimulus.

Clause 44. The apparatus of clause 1, further comprising a light source and stimulus optics to provide a binocular stimulus to the eye and a second eye of the patient, the light source and stimulus optics configured to present the binocular stimulus at an apparent distance and apparent angle between the first eye and the second eye corresponding to a near object.

Clause 45. The apparatus of clause 1, wherein the processor is configured with instructions to transmit the refractive properties of the eye for the foveal location and the non-foveal location to a remote server.

Clause 46. The apparatus of clause 45, wherein the processor is configured to transmit a map of refractive data of the eye to the remote server.

Clause 47. The apparatus of clause 1, further comprising a remote server configured to receive and store the refractive properties of the eye and to transmit the refractive properties to a remote user.

Clause 48. A method of measuring refractive properties of an eye, the method comprising: projecting a first spot of light onto a foveal location of a retina of the eye; capturing a first image of the first spot of light on the foveal location; projecting a second spot of light onto a non-foveal location of the retina; capturing a second image of the second spot of light on the non-foveal retina; and determining refraction of the eye at the foveal location of the retina and the non-foveal location of the retina.

Clause 49. The method of clause 48, wherein the projecting of the first spot of light, the capturing a first image, the projecting the second spot of light, and the capturing the second spot of light occur simultaneously.

Clause 50. The method of clause 48, wherein the projecting of the first spot of light and the capturing a first image occurs before the projecting the second spot of light and the capturing the second spot of light.

Clause 51. The method of clause 48, wherein the projecting of the first spot of light and the capturing a first image occurs after the projecting the second spot of light and the capturing the second spot of light.

Clause 52. The method of clause 48, further comprising: generating a refractive map of the eye based on the first and second images.

Clause 53. The method of clause 48, wherein the first image of the first spot comprises a plurality of images of the first spot projected onto an image sensor by a lenslet array and the second image of the second spot comprises a plurality of images of the second spot projected onto the image sensor by the lenslet array.

Clause 54. The method of clause 52, further comprising: moving the second spot to a plurality of locations of the non-foveal retina about the fovea of the retina; and capturing a plurality of third images, each of the third plurality of images corresponding to one of the plurally of locations of the second spot, and wherein generating a refractive map of the eye based on the first and second images further comprising generating the refractive map based on the first, second, and plurality of third images.

Clause 55. The method of clause 48, wherein projecting the first spot of light comprises projecting light of a first wavelength.

Clause 56. The method of clause 55, wherein projecting the second spot of light comprises projecting light of a second wavelength, different than the first wavelength.

Clause 57. The method of clause 48, further comprising determining the axial length of the eye, based on the images.

Clause 58. The apparatus of clause 57, further comprising determining the axial length of the eye at the fovea and over a range of eccentricates of up to 6 degrees from the fovea.

Clause 59. An apparatus to accommodation of an eye of a patient, the apparatus comprising: a binocular stimulus; optics coupled to the binocular stimulus configured to provide the binocular stimulus at a plurality of locations and vergences corresponding to a far vision stimulation and a near vision stimulation of the eye; and an OCT measurement beam to measure a far vision axial length of the eye in a far vision configuration of the eye and a near vision configuration configured to measure a near vision axial length of the eye; a detector to receive light from the retina from the OCT measurement beam; and a processor coupled to the detector to determine an accommodative lag of the eye corresponding to a difference between the far vision axial length and the near vision axial length less than an amount corresponding to the near vision stimulus.

Clause 60. A method of generating refractive maps of a patient's eye, the method comprising: fogging the eye with a far stimulus to provide a far vision accommodation of the eye; generating a first refractive map of the patient's eye with the far vision accommodation of the eye; stimulating the patient's eye with a near stimulus to provide a near vision accommodation of the eye; generating a second refractive map of the patient's eye with the near vision accommodation of the eye; and comparing the first refractive map of the patient's eye and the second refractive map of the patient's eye.

Clause 61. The method of clause 60, wherein the first refractive map comprises a first central refraction of a foveal location of the retina and a first plurality of non-foveal refractions corresponding to a plurality of non-foveal locations of the retina and the second refractive map comprises a second foveal refraction from the foveal location of the retina and a second plurality of non-foveal refractions corresponding to the plurality of non-foveal locations of the retina.

Clause 62. The method of clause 60, wherein a vergence of the near stimulus differs from a vergence of the far stimulus by at least two Diopters (D).

Clause 63. The method of clause 60, further comprising: determining a lag of accommodation of the patient's eye based on the first refractive map and the second refractive map.

Clause 64. The method of clause 63, wherein the lag of accommodation comprises an accommodation of the eye to the near stimulus less than an amount of the near stimulus.

Clause 65. The method of clause 64, wherein the near stimulus comprises a monocular stimulus.

Clause 66. The method of clause 64, wherein the near stimulus comprises a binocular near stimulus.

Clause 67. The method of clause 60, wherein generating the first refractive map of the patient's eye comprises: projecting a first spot of light onto the patient's central retina; capturing a first image of the first spot of light on the patient's central retina; projecting a second spot of light onto the patient's non-foveal retina; capturing a second image of the second spot of light on the patient's non-foveal retina.

Clause 68. The method of clause 60, wherein generating the second refractive map of the patient's eye comprises: projecting a first spot of light onto the patient's foveal retina; capturing a first image of the first spot of light on the patient's foveal retina; projecting a second spot of light onto the patient's non-foveal retina; capturing a second image of the second spot of light on the patient's non-foveal retina.

Clause 69. The method of clause 60, further comprising generating a prediction, diagnosis, or treatment plan based on the comparing.

Clause 70. The method of clause 69, wherein the prediction comprises a prediction of a future onset of myopia.

Clause 71. The method of clause 69, wherein the diagnosis comprises a differential lag of accommodation of the non-foveal retina of the patient.

Clause 72. The method of clause 71, wherein the differential lag of accommodation of the non-foveal retina corresponds to an amount of accommodation for the non-foveal retina less than an amount of accommodation for the foveal retina.

Clause 73. The method of clause 69, wherein the treatment plan is derived from the first and second map in order to adjust defocus of projected retinal stimulation in a treatment to decrease myopia.

Clause 74. The method of any one of the preceding method clauses, further comprising performing the processor instructions of any one of the preceding apparatus clauses.

Clause 75. The apparatus of any one of the preceding method clauses, wherein the processor is configured to perform one or more steps of a method of any one of the preceding method clauses.

Clause 76. The method or apparatus of any one of the preceding clauses wherein a foveal location of the retina comprises a central location of the retina, and a non-foveal location of the retina comprises one or more of a peripheral location of the retina or a macular location of the retina away from the fovea.

Clause 77. The method or apparatus of any one of the preceding clauses wherein a non-foveal location of the retina comprises a location of the retina away from the fovea.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. An apparatus to measure relative refractive properties of an eye, comprising:
   one or more light sources configured to emit a light;
   projection optics arranged to project the light emitted by the one or more light sources onto a foveal location of a retina and a non-foveal location of the retina;
   imaging optics arranged to generate a plurality of images from the light projected onto the foveal location of the retina and the non-foveal location of the retina;
   an imaging device configured to capture the plurality of images from the imaging optics; and
   a processor coupled to the imaging device, the processor configured to determine refractive properties of the eye for the foveal location of the retina and the non-foveal location of the retina;
   wherein the eye comprises a pupil and wherein the light to the foveal location of the retina travels through the pupil at a first angle and the light to the non-foveal location of the retina travels through the pupil at a second angle different from the first angle and wherein the refractive properties of the eye for the foveal location of the retina correspond to the light traveling to the foveal location through the pupil at the first angle and the refractive properties of the eye for the non-foveal location of the retina correspond to the light traveling through the pupil at the second angle.

2. The apparatus of claim 1, wherein the imaging optics comprise one or more of a lens or a lenslet array and wherein the plurality of images comprises one or more of a plurality images of a slit or a plurality of images of spot pattern.

3. The apparatus of claim 1, wherein the refractive properties of the eye for the foveal location of the retina comprise one or more of a first sphere, a first cylinder, a first axis, a first spherical equivalent, first coefficients of a first wavefront or a first wavefront map and the refractive properties of the eye for the non-foveal location of the retina comprise one or more of a second sphere, a second cylinder, a second axis, a second spherical equivalent, second coefficients of a second wavefront or a second wavefront map.

4. The apparatus of claim 1, wherein the processor comprises instructions to generate a refractive map of the eye based on the plurality of images captured by the imaging device, the refractive map comprising first refractive properties corresponding to the foveal location of the retina and second refractive properties corresponding to the non-foveal location of the retina.

5. The apparatus of claim 1, wherein the one or more light sources and the projection optics are arranged to project the light emitted by the one or more light sources into the eye along a first afferent light path to the foveal location of the retina and a second afferent light path to the non-foveal location of the retina.

6. The apparatus of claim 5, wherein the foveal location of the retina comprises a fovea within a macula of the central retina and wherein the non-foveal location of the retina comprises a location of the retina outside the macula.

7. The apparatus of claim 6, wherein the second afferent light path is arranged at an angle of at least 10 degrees from the angle of the first afferent light path.

8. The apparatus of claim 7, wherein the first afferent light path enters the eye along a central axis of the eye and the second afferent light path enters the eye at an angle to the central axis of the eye.

9. The apparatus of claim 6, wherein a first light from a first of the one or more light sources is projected along the first afferent light path and a second light from a second of the one or more light sources is projected along the second afferent light path.

10. The apparatus of claim 9, wherein the first light emitted by the first light source comprises a first wavelength and the second light emitted by the second light source comprises a second, different wavelength.

11. The apparatus of claim 10, wherein the first wavelength and the second wavelength comprise wavelengths in a near-infrared spectrum.

12. The apparatus of claim 10, wherein the first wavelength and the second wavelengths are separated by at least 10 nm.

13. The apparatus of claim 10, wherein the imaging device is configured to separately capture the first wavelength of the first light and the second wavelength of the second light.

14. The apparatus of claim 13, wherein the imaging device comprise a first set of pixels sensitive to the first wavelength of the first light and a second set of pixels sensitive to the second wavelength of the second light.

15. The apparatus of claim 1, wherein the imaging optics comprise a lenslet array.

16. The apparatus of claim 15, wherein the lenslet array comprises a two-dimensional array.

17. The apparatus of claim 1, wherein the lenslet array comprises a plurality of one or more of round lenslets, gradient index lenslets, diffractive lenslets or crossed cylindrical rods.

18. The apparatus of claim 1, wherein the imaging optics are arranged between the imaging device and the eye.

19. The apparatus of claim 1, wherein the imaging device comprises one or more of a CCD or CMOS imaging sensor.

* * * * *